United States Patent
Weinstein et al.

[11] Patent Number: 6,029,078
[45] Date of Patent: *Feb. 22, 2000

[54] SYSTEM FOR ASSESSING BONE CHARACTERISTICS

[75] Inventors: Joel B. Weinstein, Framington; Donald Barry, Norwood, both of Mass.

[73] Assignee: Hologic, Inc., Bedford, Mass.

[ * ] Notice: This patent is subject to a terminal disclaimer.

[21] Appl. No.: 09/013,361

[22] Filed: Jan. 23, 1998

Related U.S. Application Data

[63] Continuation of application No. 08/622,030, Mar. 26, 1996, Pat. No. 5,785,041.

[51] Int. Cl.$^7$ ................................................ A61B 5/05
[52] U.S. Cl. ................................ 600/407; 600/449
[58] Field of Search ........................... 600/407, 300, 600/437, 442, 449, 438; 422/82.05, 82.09; 436/43–46; 128/920

[56] References Cited

U.S. PATENT DOCUMENTS

| | | |
|---|---|---|
| Re. 32,782 | 11/1988 | Pratt, Jr. . |
| 3,847,141 | 11/1974 | Hoop . |
| 4,237,901 | 12/1980 | Taenzer . |
| 4,361,154 | 11/1982 | Pratt, Jr. . |
| 4,421,119 | 12/1983 | Pratt, Jr. . |
| 4,476,873 | 10/1984 | Sorenson et al. . |
| 4,668,619 | 5/1987 | Greenquist et al. . |
| 4,774,959 | 10/1988 | Palmer et al. . |
| 4,913,157 | 4/1990 | Pratt, Jr. et al. . |
| 4,941,474 | 7/1990 | Pratt, Jr. . |
| 5,014,970 | 5/1991 | Osipov . |
| 5,025,789 | 6/1991 | Hassler . |
| 5,045,480 | 9/1991 | Johnson et al. . |
| 5,119,820 | 6/1992 | Rossman et al. . |
| 5,134,999 | 8/1992 | Osipov . |
| 5,335,661 | 8/1994 | Koblanski . |
| 5,365,564 | 11/1994 | Yashida et al. ............... 378/55 |
| 5,452,722 | 9/1995 | Langton . |
| 5,769,074 | 6/1998 | Barnhill et al. ............... 600/300 |
| 5,785,041 | 7/1998 | Weinstein et al. ............. 600/407 |

FOREIGN PATENT DOCUMENTS

| | | |
|---|---|---|
| 0299906 | 1/1989 | European Pat. Off. . |
| 0312847 | 4/1989 | European Pat. Off. . |
| 0341969 | 11/1989 | European Pat. Off. . |
| 9001903 | 3/1990 | European Pat. Off. . |
| 0516353 | 12/1992 | European Pat. Off. . |
| 0576217 | 12/1993 | European Pat. Off. . |
| 0663182 | 7/1995 | European Pat. Off. . |
| 2257253A | 1/1993 | United Kingdom . |
| 2257253B | 1/1993 | United Kingdom . |
| 8002796 | 12/1980 | WIPO . |

OTHER PUBLICATIONS

IGEA, DBM Sonic 1200 Brochure (undated).
"Bone" Official Journal of the International Bone and Mineral Society, vol. 16, No. 1, pp. 246–249 Jan. 1995.
Ultrasound Assessment of Bone Fragility in the Climacteric Women by DBM Sonic 1200, Mura Marta.
Perth International Bone Meeting, Bone Fragility in the Year 2000, p. 65 (Feb. 1995).
Connective Tissue Changes in the Menopause, M. Brincat et al.
Minhorst Osteoson brochure (May 1995).
Minhorst Osteoson K IV brochure (undated).
Ultrasound for Bone Measurement, A Private Symposium, Lunar, Apr. 1992.

(List continued on next page.)

*Primary Examiner*—Francis J. Jaworski
*Attorney, Agent, or Firm*—Cooper & Dunham LLP

[57] ABSTRACT

A system and method for determining bone characteristic data is provided. The system combines a biochemical bone measuring unit with a densitometric bone measuring unit to determine the bone characteristic data. Once the bone characteristic data is ascertained, a determination of whether bone formation or bone resorption is occurring is made and future bone characteristics can be projected.

46 Claims, 19 Drawing Sheets

OTHER PUBLICATIONS

Lunar, Achilles Ultrasound Bone Densitometer brochure (undated).

Clinical Investigations, "Preliminary Evaluation of a New Ultrasound Bone Densitometer" by Belinda Lees and John C. Stevenson, Calif Tissue Int. 1993.

Report on "Ultrasonic Assessment of Bone III", May 1993. Observations at ASBMR, by G.H. Brandenburger, 1991.

"Ultrasound Measurements of the Os Calcis", by R. Mazes et al., Presented at the Third Bath Conference on Osteoporosis and Bone Mineral Measurement (Jun. 1992).

Perth International Bone Meeting, Bone Fragility in the Year 2000: Clinical Measurement, p. 63 (Feb. 1995).

Perth International Bone Meeting, Bone Fragility in the Year 2000: Clinical Measurement, p. 61 (Feb. 1995).

Abstract of "Applications of an enzyme immunoassay for a new marker of bone resorption", by M. Bonde, et al., J. Clin Endocrinol Metab Mar. 1995; 80(3) : 864–8.

Abstract of "Estimation of the effect of salmon calcitonin in established osteoporosis by biochemical bone markers", by NM Nielsen, et al., Calcif Tissue Int. Jul. 1994;55(1):8–11.

Abstract of "Postmenopausal bone loss and the risk of osteoporosis", by C. Christiansen, Osteoporos Int. 1994;4 Suppl 1:47–51.

Abstract of "The diagnostic validity of urinary free pyridinolines to identify women at risk of osteoporosis", by C. Fledelius, et al., Calcif Tissue Int May 1994; 54(5):381–4.

Abstract of "The carboxy–terminal pyridinoline cross–linked telopeptide of type I collagen in serum as a marker of bone resorption: the effect of nandrolone decanoate and hormone replacement therapy", by C. Hassager, et al., Calcif Tissue Int Jan. 1994;54(1):30–3.

"Osteoporosis: Diagnosis and Management Today and Tomorrow", by C. Christiansen, Bone, vol. 17, No. 5, Suppl. Nov. 1995:513S–516S.

"Postmenopausal Bone Loss and the risk of Osteoporosis", by C. Christiansen, Osteoporosis Int. vol. 4 (1994) Suppl. 1:S47–51.

"Biochemical Markers of Bone Turnover to Monitor the Bone Response to Postmenopausal Hormone Replacement Therapy", by B.J. Riis, et al., Osteoporosis Int. vol. 5, No. 4 (1995) pp. 276–280.

SYSTEM FOR ASSESSING BONE CHARACTERISTICS

This is a continuation of application Ser. No. 08/622,030 filed Mar. 26, 1996 and now U.S. Pat. No. 5,785,041.

BACKGROUND

1. Field of the Invention

The present invention relates to systems for assessing bone characteristics. More particularly, the present invention relates to a system that performs biochemical and densitometric assessments of bone material to provide practitioners with bone characteristic data for evaluation of a patient's bone material for diagnosis and management of bone related disease.

2. Description of the Related Art

The diagnosis and management of bone related disease, such as osteoporosis, typically requires information about bone turnover and bone mass. Determinations of bone turnover have historically been performed utilizing standard serum and/or urine laboratory tests including fasting calcium/creatinine, hydroxyproline, alkaline phosphatase and/or osteocalcin/bone growth protein utilizing standard high pressure liquid chromatography (HPLC) techniques. To illustrate, whenever bone formation occurs (calcium deposition) or bone resorption occurs (calcium breakdown), various chemical reactions occur within the body which elevate the presence of certain indicators in the blood and urine suggesting changes in the calcium/bone mineral status.

Recently, several new bone specific assays have been developed which enable bone turnover to be evaluated with an ELISA/EMIT immunoassay format. Descriptions of these immunoassay formats can be found in U.S. Pat. Nos. 5,973,666, 5,320,970, 5,300,434 and 5,140,103. The labeling for the new assays utilize a biochemical marker to quantify bone resorption and/or formation and permit a trained practitioner to assess bone turnover.

Bone mass determinations, on the other hand, have been traditionally performed by using various x-ray based techniques including single and dual-photon absorptiometry (SPA and DPA), quantitative computed tomography (QCT), and dual-energy absorptiometry (DXA).

To reduce the time necessary to determine if bone resorption or formation is occurring and to permit a practitioner to project future bone characteristics, a system which combines a biochemical bone measuring system that measures, for example, bone turnover, with a densitometric bone measuring system that measures, for example, bone density is desirable.

Further, the x-ray based equipment emits ionized radiation in the form of x-rays and requires a licensed technician to operate the equipment. In addition, this equipment is structurally large and constructed to house, for example, an x-ray source and an x-ray detector, and provides a large table area to position the patient for examination. As a result, such x-ray based equipment occupies a large floor area. In addition, since x-rays are emitted by such equipment, certain safety precautions must be followed to limit human exposure to the emitted rays.

High frequency ultrasound has recently become an alternative technique for determining preliminary assessments of bone status. Measuring the bone density with ultrasound is currently more desirable over some of the above mentioned techniques since there is no ionizing radiation in the form of x-rays produced by ultrasound. As a result, a licensed x-ray technician does not have to be employed to operate the ultrasonic measuring equipment and the environment where the instrument is located and operated is not strictly regulated. In addition, ultrasonic measuring equipment can be manufactured significantly smaller in size and weight than the above-mentioned x-ray type bone density measurement equipment and is suitable for installation in private offices or medical facilities where space is typically at a premium.

The parameters that can be determined using ultrasound include the speed-of-sound, the attenuation of the ultrasound signal and/or combinations of the above as it penetrates bone and tissue. These parameters provide general characteristics relating to bone density and the risk of future fracture.

Although the above described assay techniques provide a practitioner with information regarding the rate of bone resorption or formation, the results from such techniques are of limited value unless a baseline level of bone mass can also be established. Measuring bone density provides practitioners with baseline bone density information and after successive measurements over a period of time, e.g., one year, may also permit the practitioner to determine if bone resorption or bone formation is occurring. However, this process takes a period of time (nominally, approximately one year) to determine if there is bone resorption or formation occurring. Biochemical markers which evaluate physiological status directly are capable of evaluating the change in the amount of bone formation or resorption, for example, in response to therapy, in a matter of months. Thus, to quickly and accurately obtain an assessment of bone formation or resorption a practitioner typically utilizes both measurements to obtain the necessary bone characteristic data.

Thus, a need exists for a bone measuring system capable of performing various types of assessments of bone material and providing a practitioner with bone characteristic data in the form of, for example, graphical display results, to permit the practitioner to diagnose and manage bone related disease.

A need also exists for a compact and inexpensive system that may be installed in a practitioner's office or like location and that reduces the time necessary to determine bone resorption or formation and to permit a practitioner to diagnose and manage bone related diseases.

SUMMARY

The present invention provides a biochemical bone measuring unit and a densitometric bone measuring unit to form a bone measuring system that performs biochemical and densitometric assessments of bone material. The system of the present invention provides practitioners with bone characteristic data to evaluate bone status, and in some instances provides a prognosis as to future bone characteristics so as to enable the practitioner to manage bone related disease.

In one embodiment, the system of the present invention combines the biochemical bone measuring unit and the densitometric bone measuring unit into a single housing which is compact and capable of being installed in a practitioner's office.

In an alternative embodiment, the densitometric and biochemical units are connected to each other via standard data communication circuitry and either the densitometric bone measuring unit or the biochemical bone measuring unit has a controller that combines the measurements from each unit to provide practitioners with the bone characteristic data.

In another alternative embodiment, the biochemical bone measuring unit and the densitometric bone measuring unit may be individual units that separately perform biochemical and densitometric bone assessments. The results of the individual assessments can be manually or automatically combined to provide practitioners with the bone characteristic data.

In another alternative embodiment, the biochemical bone measuring unit and the densitometric bone measuring unit may be individual units that separately perform biochemical and densitometric bone assessments and transfer data from such assessments to a separate personal computer. The personal computer combines the measurements from each unit and performs the bone assessment to provide practitioners with the bone characteristic data. In one embodiment, the single unit system includes a housing having a bone mass measurement system and a sample access port, a display mounted to the housing such that a display surface of the display is visible through the housing. Strip reader circuitry is located within the housing and is configured to direct light to a strip sample, to filter light reflected by the strip sample such that at least one predefined color wavelength is permitted to pass, and to detect the filtered light and generate a detected sample signal. The strip reader circuit and the sample access port form the biochemical bone measuring unit (or system). The single unit bone measuring system also includes the densitometric bone measuring unit (or system) positioned within the housing and configured to generate bone mass data. The densitometric bone measuring unit preferably includes a pair of adjustable ultrasonic transducers, and associated encoders and drive mechanisms to move the transducers. A processor is located within the housing and is coupled to the strip reader circuit and the ultrasonic transducers, the encoders and the transducer drive mechanisms. The processor is provided to receive a detected sample signal from the strip reader circuit and to generate bone turnover data from the detected sample signal. The processor also controls the operation of the ultrasonic transducers and determines bone mass data. The processor then processes the bone turnover data and the bone mass data to determine if bone formation or resorption is occurring (i.e., performs the bone assessment). Once the current bone density and the bone turnover data are ascertained and a determination of whether there is bone formation or resorption is made, then the processor can project future bone characteristics and provide the results on the display or by a printout. Such results may include a graph of bone density verses time, or a listing of bone density values over a period of time.

In an alternative embodiment, the bone measuring system of the present invention is constructed from individual components and includes a controller having memory and data communication capability, a biochemical bone measuring unit coupled to the controller, and a densitometric bone measuring unit coupled to the controller. In this embodiment, the controller performs similar operations as those described above.

The present invention contemplates different embodiments for the individual biochemical bone measuring unit and the densitometric bone measuring unit. One embodiment of the biochemical bone measuring unit includes a housing having at least one access port adapted to receive a strip sample, or to direct a bodily fluid sample onto one or more strip tests or a receptor pad in the housing, at least one strip sample reading circuit located within the housing and configured to direct light to the strip sample, to filter light reflected by the strip sample so that at least one predefined color wavelength is permitted to pass, and to detect the filtered light and generate a detected sample signal, and a processor located within the housing and coupled to the at least one strip sample reading circuit. The processor is preferably configured to receive the detected sample signal, to generate bone turnover data from the detected sample signal and to display the bone turnover data. The biochemical bone measuring unit may optionally include a display mounted to the housing so that a display surface of the display is visible through the housing. The housing can be configured to be hand-held having dimensions similar to those of, for example, a hand-held calculator.

The strip sample reading circuit uses a light emitting source, an optical filter and a light receiving element to read a color marker on a strip sample containing the immunoassay. The light emitting source is configured to emit light (e.g., laser, incandescent, fluorescent, light emitting diode) toward the strip sample and the optical filter is configured to permit predefined color wavelengths reflected from a sample portion of the strip sample to pass therethrough. A light detecting element receives the filtered reflected light and generates a sample detected signal for transfer to the processor for an assessment of bone turnover.

In an alternative embodiment, the strip sample includes a reference portion in addition to the sample portion, and the strip sample reading circuit includes a second optical filter and a second light detecting element. A second optical signal is configured to pass predefined color wavelengths of light reflected from the reference portion of the strip sample and the second light detecting element receives the filtered reflected light and generates a reference signal for transfer to the processor. The reference signal provides a control value as an indication of the quality of the strip sample.

In another alternative embodiment, the strip sample reading circuit includes an optical filter positioned in front of a light source and the light emitted from the strip sample passes through a second filter so that fluorescent light from the sample impinges a light detecting element and generates a signal for transfer to the processor.

The densitometric bone measuring unit may be, for example, an ultrasound based unit or an x-ray based unit. One embodiment for an ultrasound bone measuring unit includes a pair of ultrasonic transducers which are movable relative to each other, associated drive mechanism that moves the transducers, and encoder circuitry and temperature sensors to measure transducer characteristics for calculation of bone density. A rack and pinion type of drive mechanism is contemplated. However, other known types of drive mechanisms may be used to move the transducers. A controller, such as a microprocessor and associated memory, is provided to control the operation of the transducers, drive mechanism, encoders and sensors and to determine bone density.

The present invention also provides a method for determining and displaying bone characteristic data. The method includes the steps of reading a strip sample by directing light toward the strip sample and detecting light reflected or emitted from the strip sample and generating signal data indicative of a concentration of a biochemical analyte or a combination of analytes and defining bone turnover data associated with a patient, obtaining bone density data for the patient, and determining whether bone formation or resorption is occurring based on the bone turnover data, and projecting future bone characteristics based on the bone density data and the bone turnover data. The determinations of bone turnover and bone density can be graphically displayed on a computer monitor in the form of charts and graphs.

BRIEF DESCRIPTION OF THE DRAWINGS

Preferred embodiments of the invention are described hereinbelow with reference to the drawings wherein.

DETAILED DESCRIPTION

The bone measuring system of the present invention combines a biochemical bone measuring unit and a densitometric bone measuring unit to form a system that performs biochemical and densitometric assessments of bone material. Such assessments provide practitioners with bone characteristic data to evaluate bone status, and in some instances, to provide a prognosis of future bone formation or resorption.

In the embodiments discussed hereinbelow, the bone characteristic data includes bone turnover data which is measured by the biochemical bone measuring unit, and bone mass data which is measured by the densitometric bone measuring unit.

Biochemical assessments of bone characteristics can be made by detecting characteristics from, for example, an assay based strip sample. The strip sample is typically the result of a quantitative in-vitro diagnostic strip test performed on a bodily fluid sample such as blood or urine. However, other techniques or methods may also be utilized for biochemical assessments. For example, the techniques contemplated include a solid-phase immunoassay technique, a western blotting technique and fluorescent microscopy technique. Various types of assays, such as chemical, enzymatic, and immunochemical assays, may be used on the strip sample. Chemical assays may detect, for example, phosphorous and/or calcium. Enzymatic assays may detect, for example, the enzyme action of alkaline phosphatase. Immunochemical assays may detect biologic compounds by monoclonal or polyclonal antibodies or specific receptor proteins.

The strip test incorporates one or more markers evaluating bone resorption, bone formation or a combination of both attached to a strip backing and a color marker bound to the bone formation or resorption markers. The strip test may be configured in various shapes including, for example, rectangular, square, circular, and triangular shapes. The strip test also includes receptor pads used to absorb bodily fluids. Preferably, the strip test employs a monoclonal or polyclonal antibody or antibodies to capture and detect an analyte. For example, bone-specific alkaline phosphatase, osteocalcin, or propeptides of type-I procollagen can be used as markers for determining bone formation, and/or telopeptide of type-I collagen, pyridinoline, deoxypyridinoline, or hydroxyproline can be used as markers for determining bone resorption. These antibodies, can be pre-applied to the strip test backing surface. A strip sample typically includes the strip test and the bodily fluid. Preferably, when a bodily fluid sample is applied to the strip test, the strip sample provides an optical scaling response proportional to the concentration of the analyte on the strip sample. The optical scale assignment provides quantitative information about the amount of analyte on the strip sample which indicates whether bone resorption or formation is occurring depending upon which of the markers are attached to the strip test backing.

Figure 1:
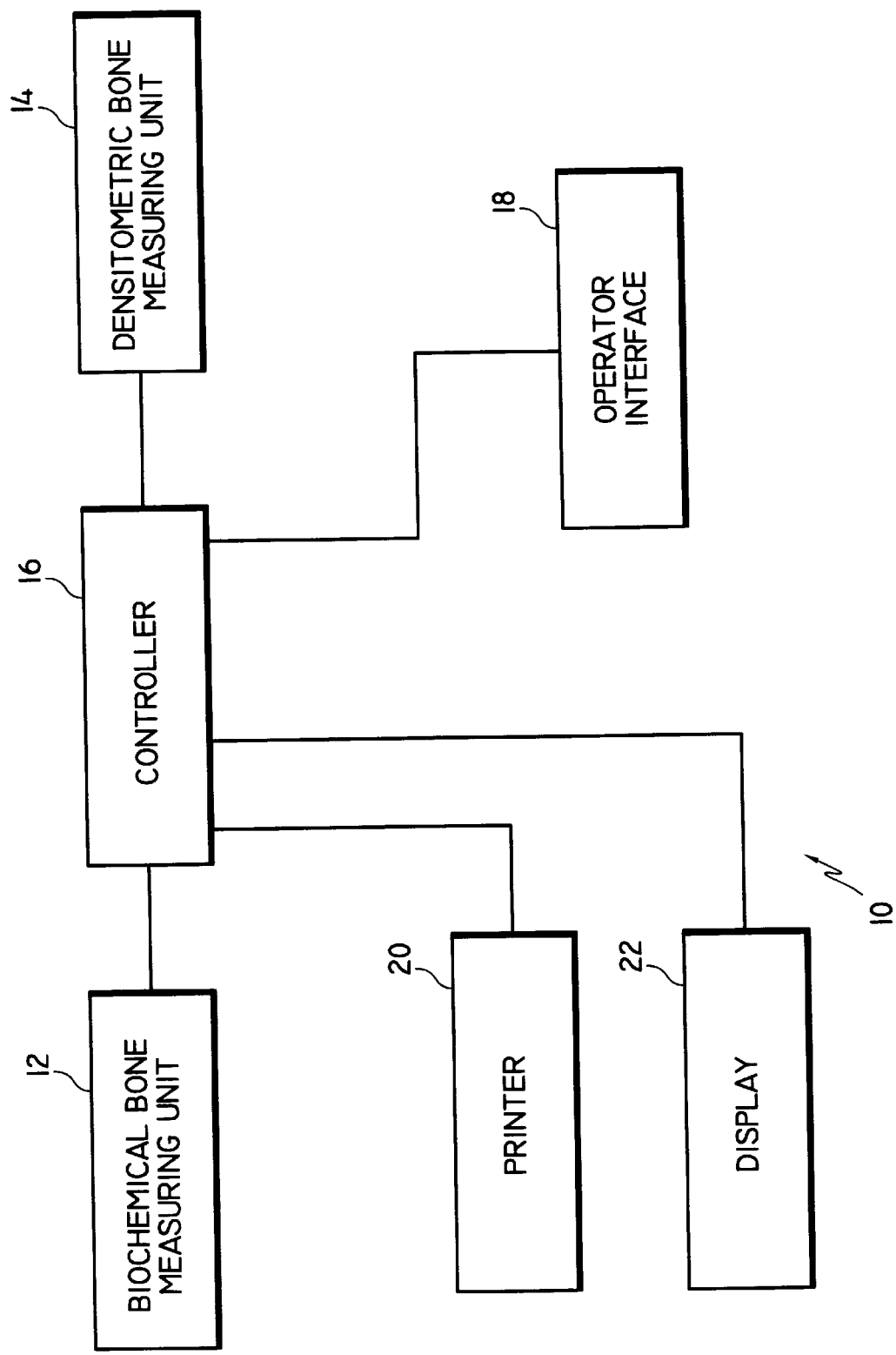
FIG. 1 is a block diagram of one embodiment of a bone measuring system according to the present invention.

Referring to FIG. 1, a block diagram of an alternative embodiment of the bone measuring system 10 of the present invention is shown. The bone measuring system 10 includes a biochemical bone measuring unit 12 and a densitometric bone measuring unit 14 connected to a controller 16. The biochemical bone measuring unit 12 provides the controller 16 with detected signals representing, for example, bone turnover data. The densitometric bone measuring unit 14 provides the controller 16 with detected signals representing, for example, bone density data. The controller 16 then processes the signals from each unit and determines, for example, whether bone formation or resorption is occurring. After the controller determines if bone formation or resorption is occurring, results of the assessment can be provided via printer 20 and paper port 21, or display 22. An operator interface 18 is connected to controller 16 to permit user interaction with the controller.

Figure 2:
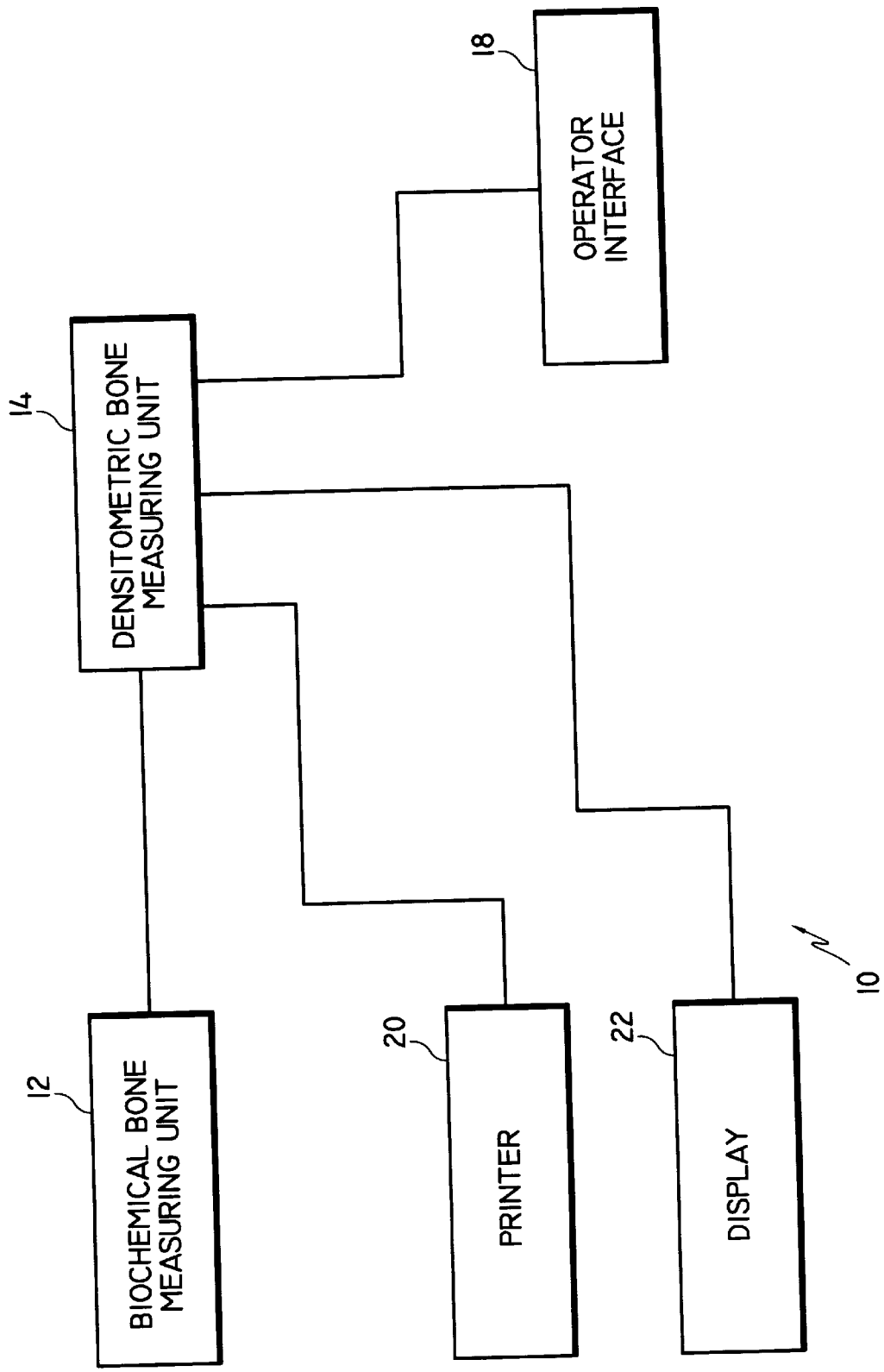
FIG. 2 is a block diagram of an alternative embodiment of the bone measuring system according to the present invention.

Referring to FIG. 2, a block diagram of an alternative embodiment of the bone measuring system of the present invention is shown. In this embodiment, the bone measuring system 10 includes a biochemical bone measuring unit 12 connected to a densitometric bone measuring unit 14 which includes the controller 16 that receives information from the biochemical bone measuring unit as well as the densitometric bone measuring unit 14.

Figure 3:
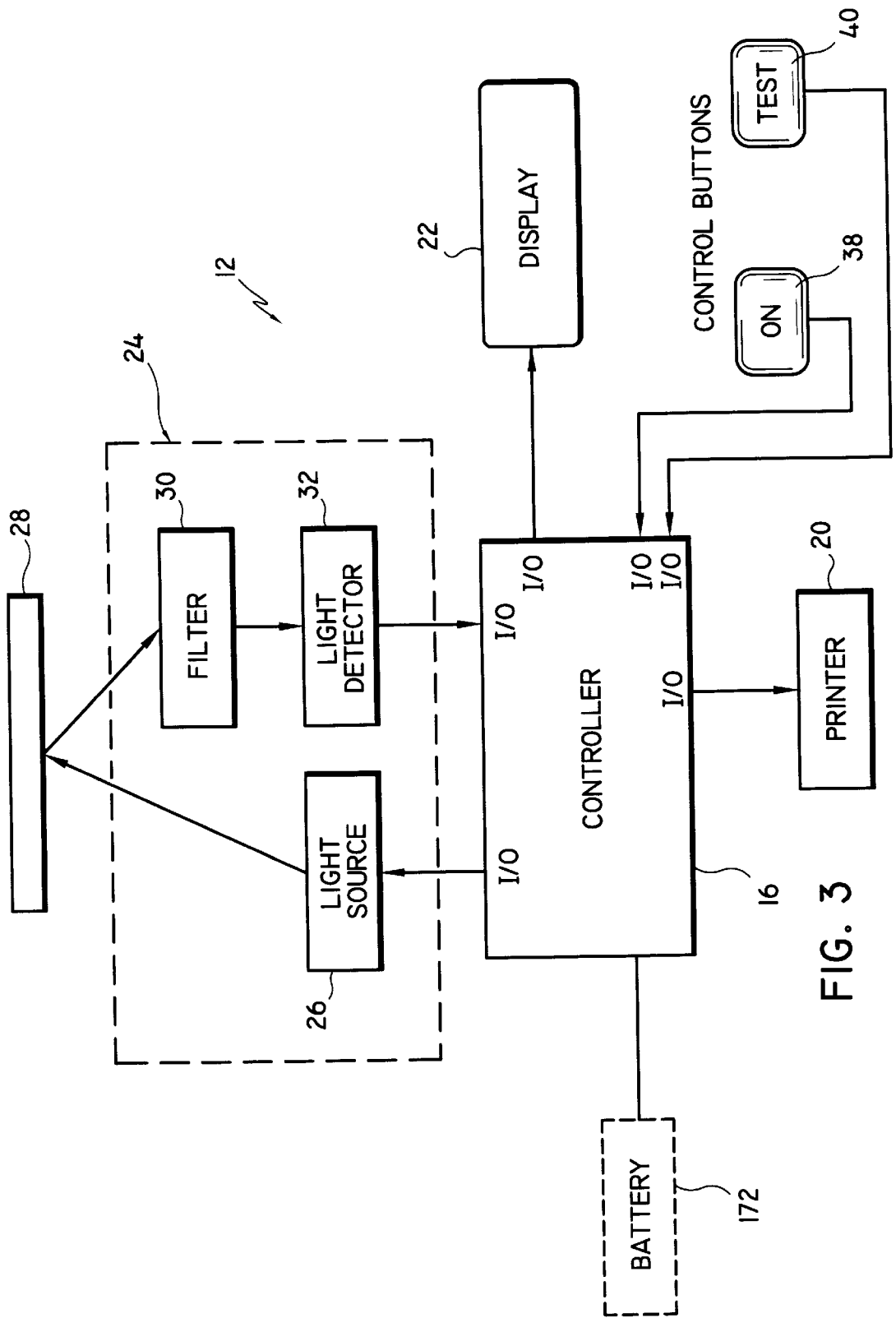
FIG. 3 is a block diagram of the components of a biochemical bone measuring unit of the system of FIGS. 1 and 2 illustrating an exemplary strip sample reading circuit.

Referring to FIG. 3, the biochemical bone measuring unit 12 of the system 10 of the present invention includes strip sample reading circuit 24 that measures the optical scaling response of the strip sample. The strip sample reading circuit 24 includes a light source 26 which emits light towards a sample strip 28 which is inserted into a access port 29, seen in FIG. 9. Suitable light sources include light-emitting and laser diodes, and incandescent and fluorescent lamps. Light reflected from the sample strip 28 is filtered by optical filter 30 and impinges light detector 32. A suitable optical filter is a color filter which permits predetermined color wavelengths to pass therethrough. For example, the optical filter 30 may be a polarized lens disposed at a predetermined angle to permit certain wavelengths to pass. The output of the light detector may be an analog or digital signal which is transferred to the controller 16. A suitable light detector is a photodiode.

If the output of the light detector is an analog signal then the controller 16 may include an analog-to-digital converter to convert the analog detector signal to a digital format for subsequent processing. Alternatively, the light detector may include an analog-to-digital converter and drive circuitry which performs the signal conversion and transfers the signal to the processor.

Figure 4:
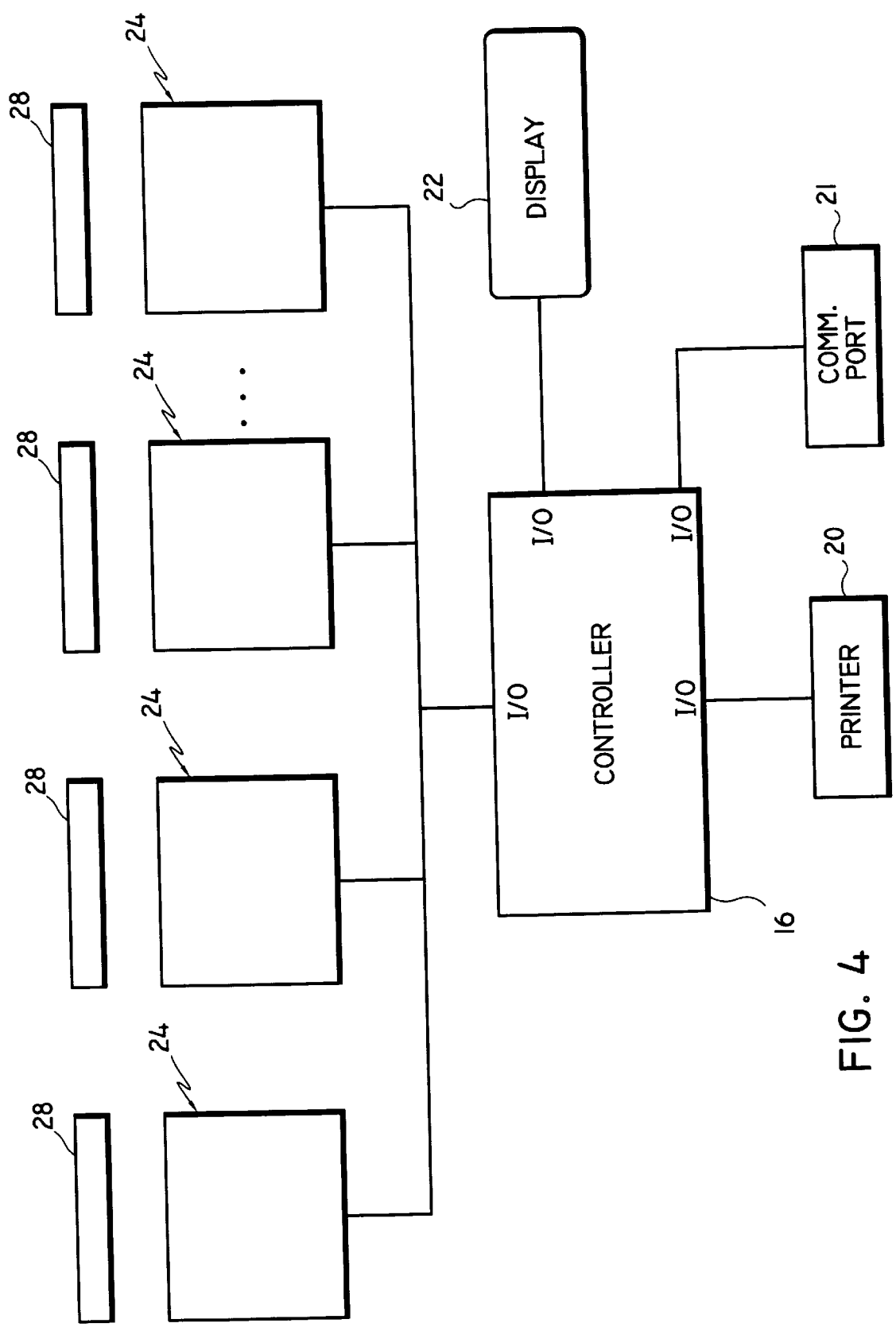
FIG. 4 is a block diagram of an alternative embodiment of the components of a biochemical bone measuring unit of the system of FIGS. 1 and 2, illustrating multiple strip sample reading circuits.

FIG. 4 shows an embodiment where the biochemical bone measuring unit 12 includes a plurality of strip sample reading circuits 24 aligned with a plurality of strip samples and connected to the controller 16. In this embodiment, the plurality of strip samples can be read and the information obtained therefrom can be used to determine bone turnover. For example, one strip test may have bone formation markers attached thereto and the strip sample represents bone formation, and another strip test may have bone resorption markers attached thereto and the strip sample represents bone resorption. The ratio between the measured value from the bone formation strip test and the measured value from the bone resorption strip test provides bone turnover data. When the bodily fluids sample is urine, the measured bone formation and/or resorption values may vary depending upon the time period between urine secretions by the patient. To compensate for such variations a creatinine normalization technique may be implemented. Creatinine normalization provides a baseline marker for urine concentration and if the creatinine concentration level is high the bone marker concentration level may be high resulting in an inaccurate estimate of bone formation or resorption. To compensate for variations in bone formation and/or resorption values, a ratio of the bone marker concentration level to the creatinine concentration level is obtained to determine whether bone formation or resorption is occurring. To determine the creatinine concentration level a color marker that binds with creatinine can be attached to a strip test backing and when combined with the urine strip sample can then be measured by the strip sample reading circuit. The controller in the biochemical bone measuring unit can then determine the ratio of bone marker concentration level to the creatinine concentration level to more accurately determine bone turnover.

Figure 5:
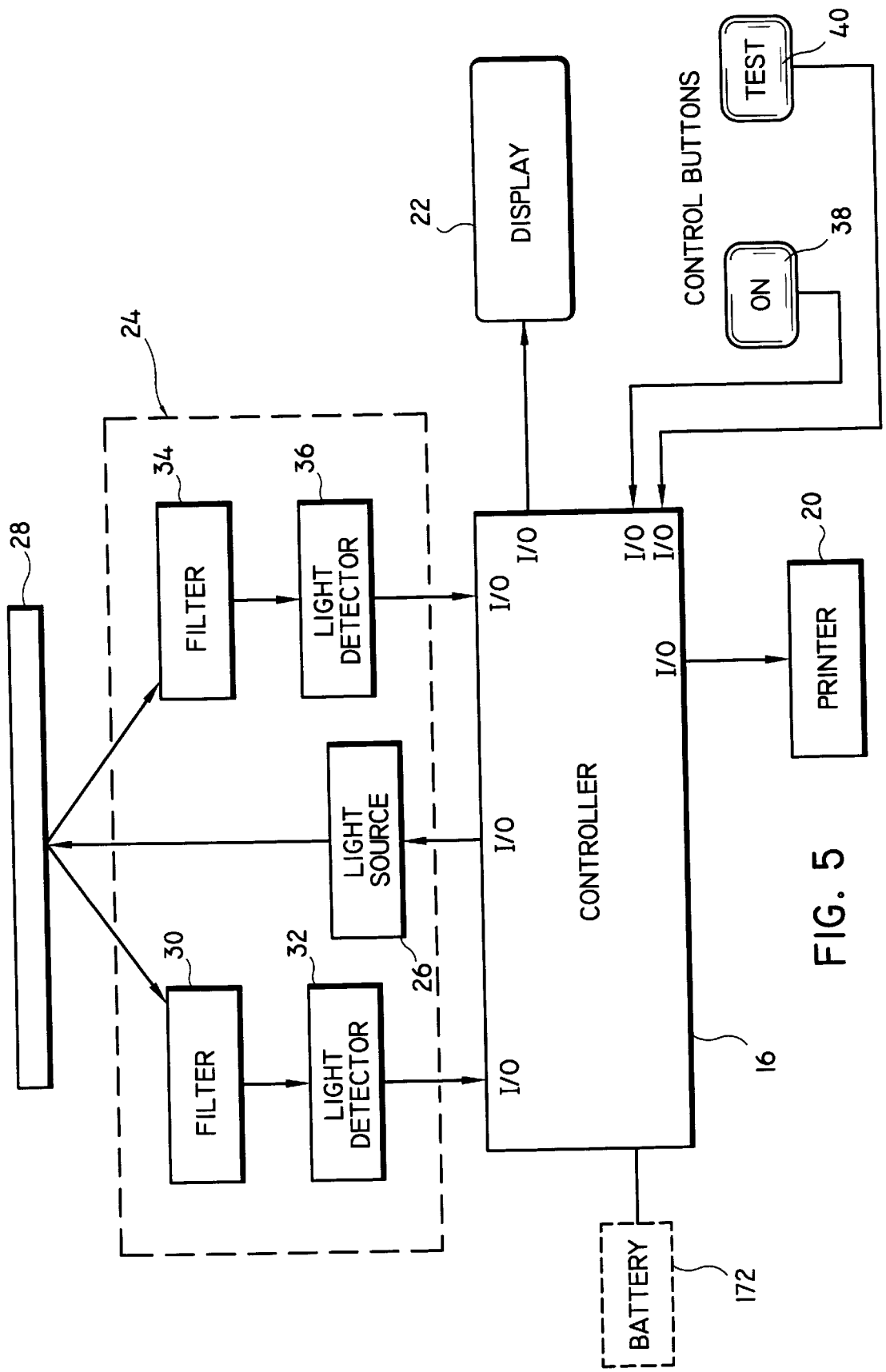
FIG. 5 is a block diagram of an alternative embodiment of the components of a biochemical bone measuring unit of the system of FIGS. 1 and 2, illustrating a strip sample reading circuit configured to read two markers on a strip sample.

Referring to FIG. 5, an alternative embodiment of the strip sample reading circuit 24 is provided. In this embodiment, a second optical filter 34, which is similar to optical filter 30, and a second light detector 36 are provided to read a reference sample portion on the strip sample 28 simultaneously when reading the portion of the strip sample to be tested. The reference sample provides a known reflectance value which may be utilized to perform a system calibration or to verify the quality of the strip sample being measured (e.g., to determine if the strip sample is stale).

Figure 6:
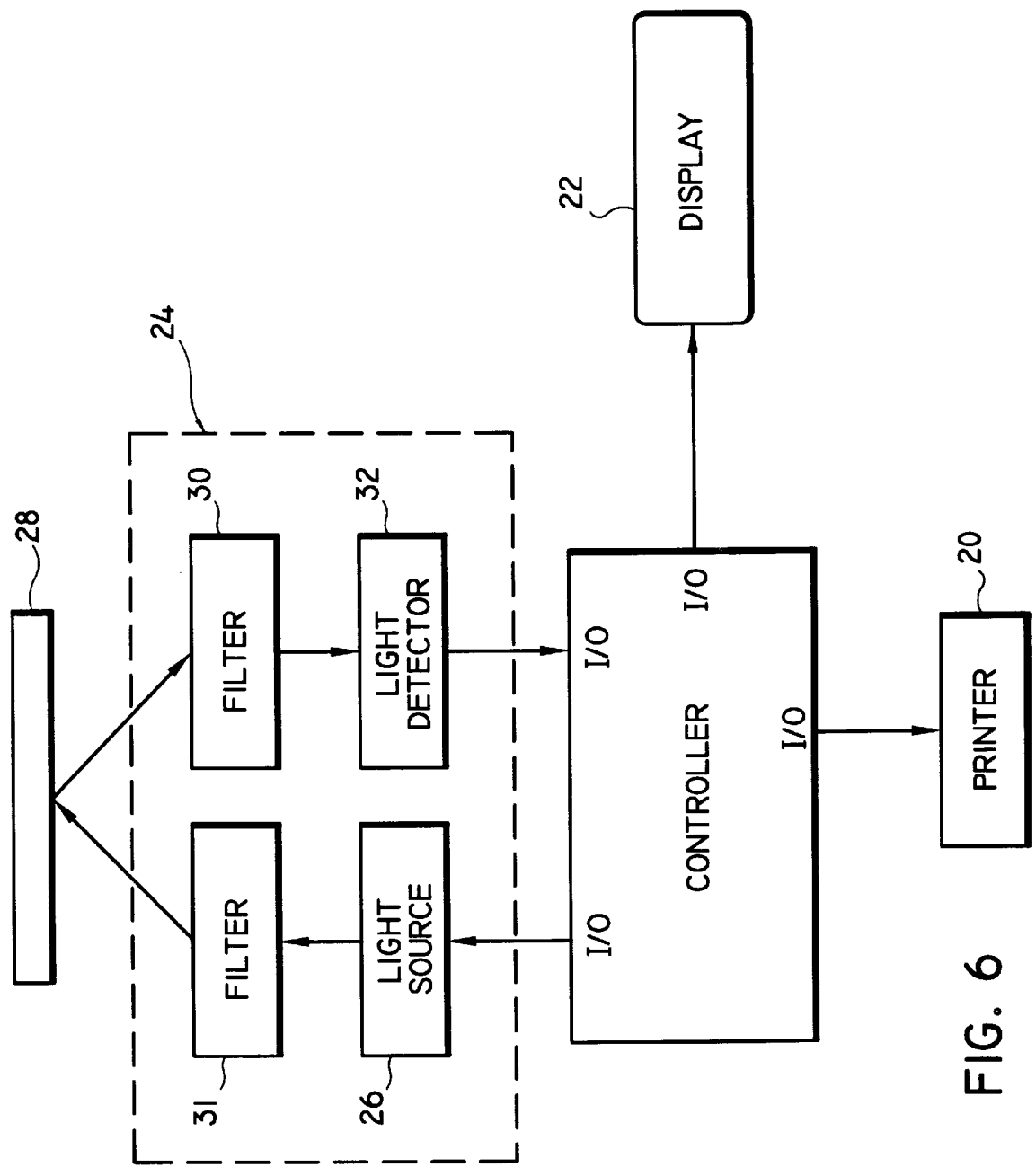
FIG. 6 is a block diagram of an alternative embodiment of the components of a biochemical bone measuring unit of the system of FIGS. 1 and 2, illustrating a strip sample reading circuit configured to use fluorescent light to read a strip sample.

FIG. 6 shows an embodiment of the bone measuring unit 12 having a fluorescent light source 26 that emits light through filter 31 toward the strip sample. The filter 31 is used to filter the light from the source 26 so that only excitation light passes therethrough. Filter 30 is used to filter the light emitted from the strip sample so that only fluorescent light passes therethrough. In this embodiment, the fluorescent microscopy technique is used to perform the biochemical assessment of the bone material.

Figure 7:
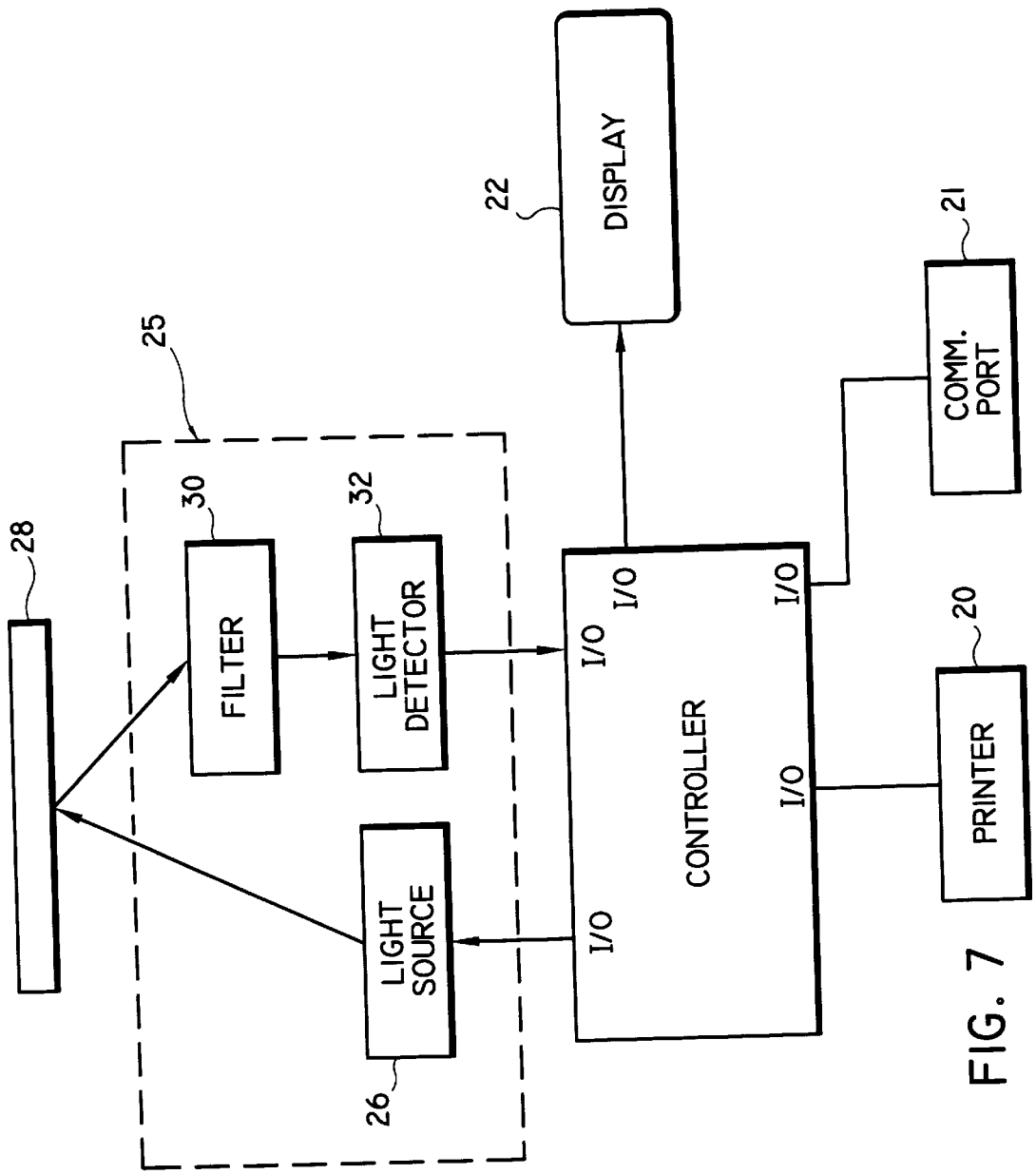
FIG. 7 is a block diagram of an alternative embodiment of the components of a biochemical bone measuring unit of the system of FIGS. 1 and 2, illustrating a disposable strip sample and strip sample reading circuit.
Figure 13:
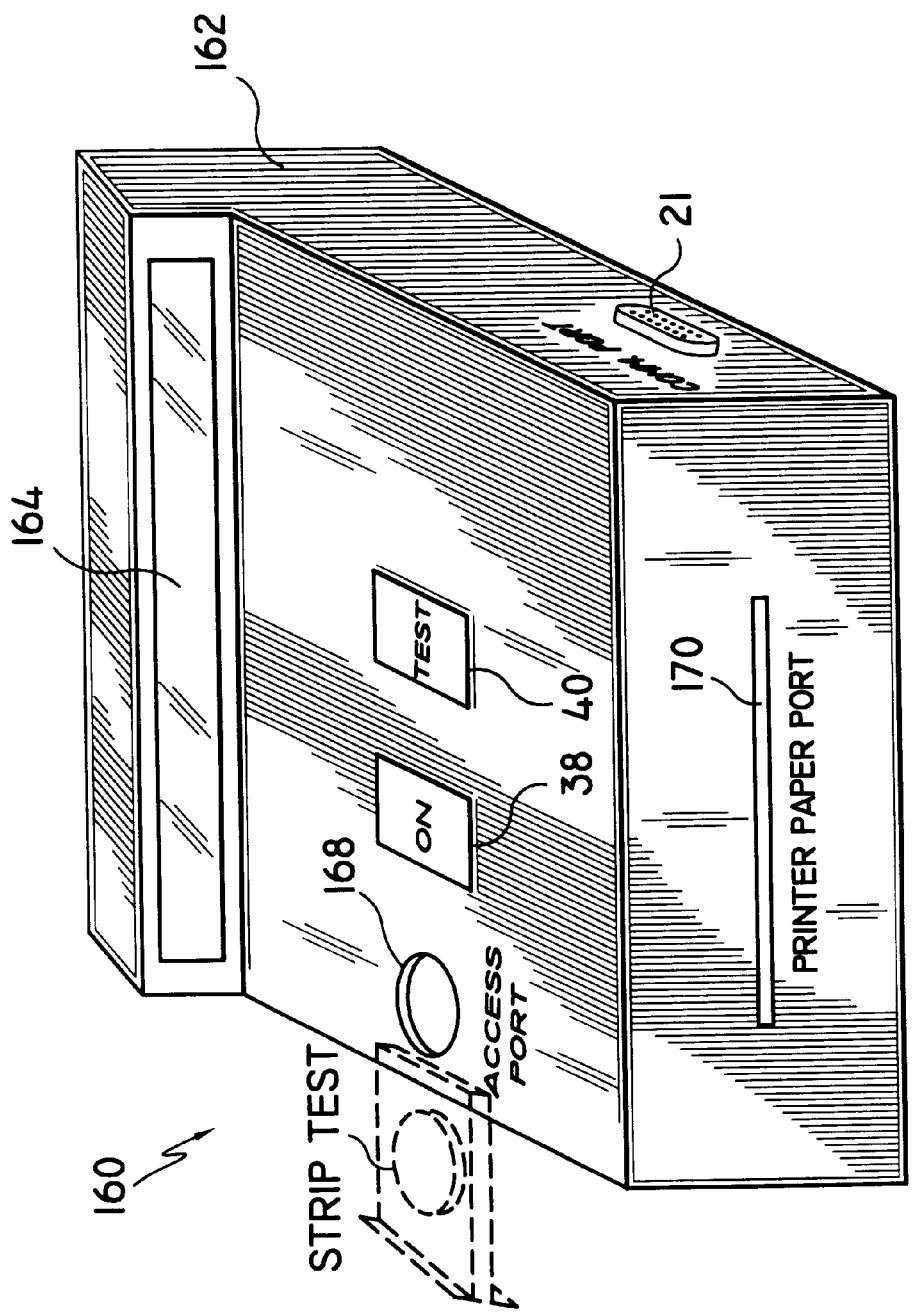
FIG. 13 is a perspective view of a biochemical bone measuring unit according to the present invention.

FIG. 7 shows an embodiment of the bone measuring unit 12 having a disposable reader portion 25 that includes strip sample reading circuit 24 and strip sample 28. In this embodiment, the strip sample is internal to the unit 12 and a bodily fluid sample is deposited onto the strip test. After a sufficient time has elapsed to allow the analytes in the sample to interact with the strip test, the strip sample reading circuit is activated to measure, for example, the concentration of analytes. After a bodily fluid sample is tested, the disposable reader portion 25 is removed from the unit and a new disposable reader portion is inserted for testing another bodily fluid sample, as seen in FIG. 13. As discussed above, the controller 16 processes the detected signals from the strip sample reading circuit and determines bone turnover. As noted, the controller 16 can format the detected signals for transmission to, for example, the densitometric bone measuring unit 14 via communication port 21. Known data transmission techniques may be used to transfer the data from the biochemical bone measuring unit.

During operation of the biochemical bone measuring unit 12, seen in FIG. 3, the bone measuring system 10 can be turned on by depressing button 38 and then a strip sample 28 is inserted into strip access port 29. The measurement function can then be activated by depressing button 40. When the measurement function is activated, the controller 16 sends a signal to light source 26 which emits light toward the strip sample 28. Light which impinges the strip sample is at least partially reflected toward optical filter 30 which permits predefined wavelengths of light reflected from the strip sample to pass to the light detector 32. The light detector then generates a sample detected signal representing the color reflectance value of the reflected light and transfers the sample detected signal to the controller 16. The controller 16 receives the sample detected signal and determines the bone turnover rate. For example, as the color increases the sample detected signal decreases indicating increased bone turnover, or as the color decreases the sample detected signal increases indicating decreased bone turnover. The resulting bone turnover data may then be displayed by display 22 or provided as a hard copy by the printer 20.

In the embodiment of FIG. 5, the reflected light from the strip sample is also filtered by optical filter 34 and is passed to the light detector 36. The light detector 36 responds by generating a reference detected signal which is related to the color detected. The reference detected signal is then transferred to the controller 16 and converted to a digital format using for example, an analog-to-digital converter. Controller 16 receives the reference signal and compares the reference signal to a control reflectance value stored in the controller memory. For example, as the difference between the reference signal and the sample detected signal increases the sample detected signal decreases indicating increased bone turnover, or as the difference between the reference signal and the sample detected signal decreases the sample detected signal increases indicating decreased bone turnover. If the reference value is not equal to or within a predefined tolerance (e.g., ±10 percent) of the control reflectance value, the controller may then discard the sample detected signal generated by light detector 32 and discontinue the measurement procedure. Further, the controller may display that a error has occurred in the biochemical bone measuring unit 12, or that the strip sample 28 is unsuitable for testing. If the reference value is equal to or within the predefined tolerance then the processor continues the measurement procedure.

The above-described biochemical bone measuring unit 12 performs the biochemical assessment of bone characteristics. As noted above, the system 10 of the present invention performs biochemical and densitometric assessments of bone characteristics.

The densitometric bone measuring unit 14 may use ultrasound to measure broadband ultrasound attenuation values and speed of sound to determine bone density. However, other types of densitometric systems are also contemplated. For example, the densitometric bone measuring system may use x-rays to measure bone density. An example of an x-ray based densitometric bone measuring system using a pencil beam to measure bone density is described in U.S. Pat. No. 4,811,373 and is incorporated herein in its entirety by reference. An example of an x-ray based densitometric bone measuring system using a fan beam of x-rays to measure bone density is described in U.S. patent application Ser. No. 08/345,069 filed on Nov. 24, 1994 and is incorporated herein in its entirety by reference.

Figure 8:
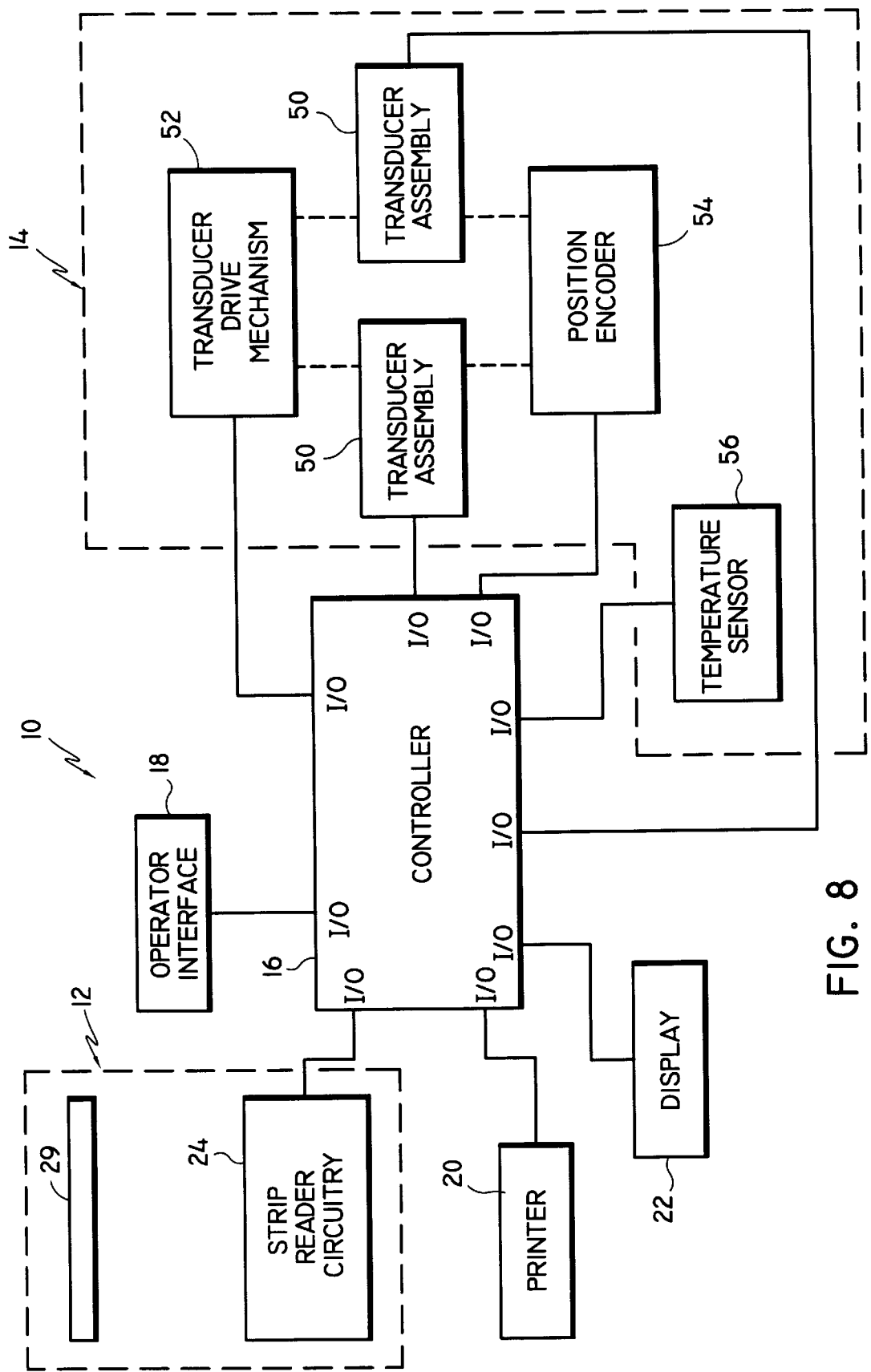
FIG. 8 is a block diagram of the system of the present invention, and illustrating a biochemical bone measuring unit and ultrasound densitometric bone measuring unit connected to the controller.

FIG. 8 is a block diagram of the bone measuring system 10 with a biochemical bone measuring unit 12 and an ultrasound bone measuring unit 14. The ultrasound bone measuring unit 14 generally includes a pair of transducer assemblies 50 connected to a transducer drive mechanism 52 that automatically positions the transducer assemblies 50 against a body part of a patient, e.g. the patient's heel, with sufficient pressure to insure ultrasonic coupling. A position encoder 54 is used to determine the position of the transducer assemblies 50. A temperature sensor 56 is provided to improve the accuracy of the position encoder measurements and to correct for temperature dependent inaccuracies in the ultrasound measurements. A more detailed description of an ultrasound densitometric bone measuring unit is described in copending application Ser. No. 08/477,580, filed Jun. 7, 1995, which is incorporated herein in its entirety by reference.

Figure 9:
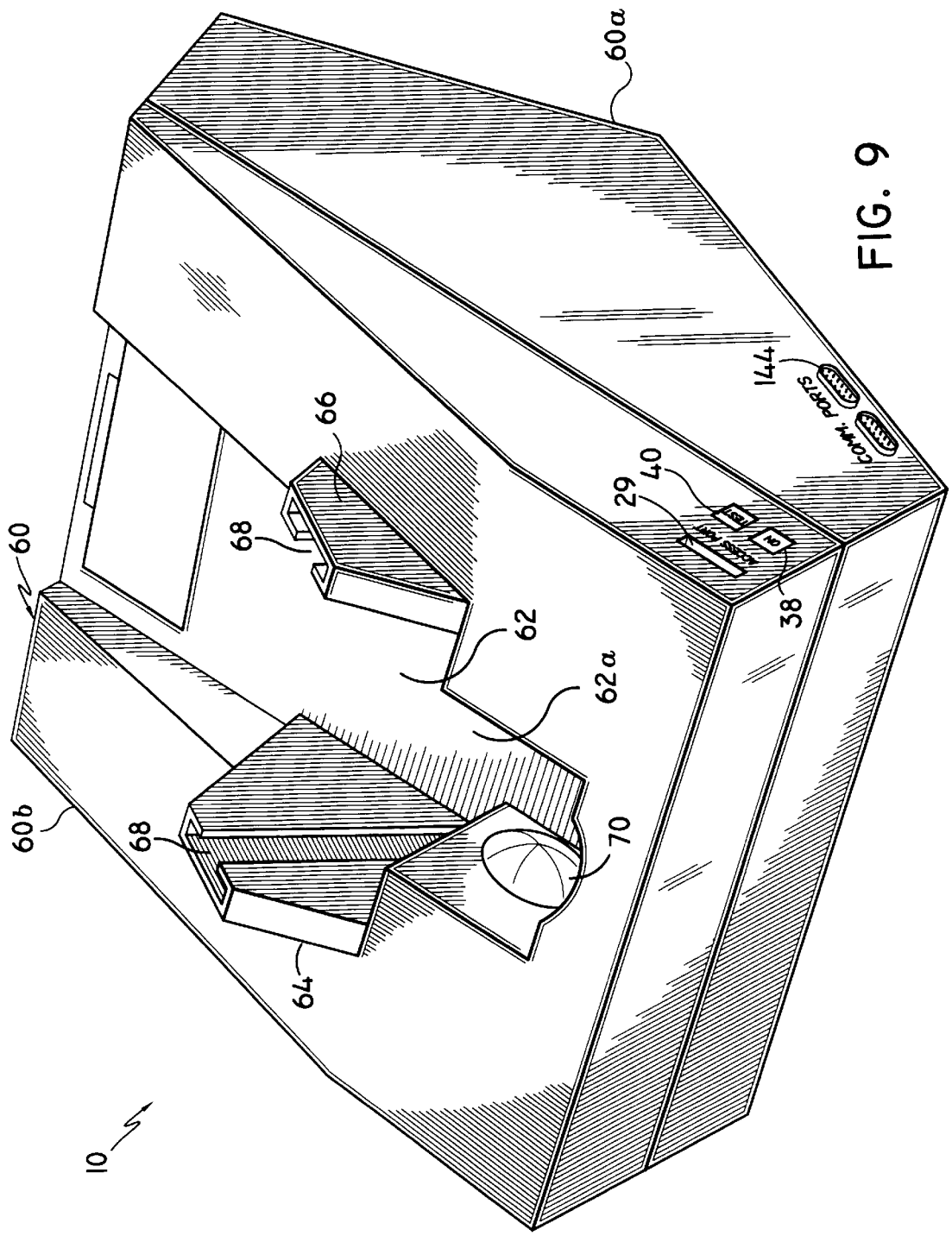
FIG. 9 is a perspective view of one embodiment of an integral bone measuring system according to the present invention, and illustrating the biochemical bone measuring unit and the densitometric bone measuring unit in a compact housing.
Figure 10:
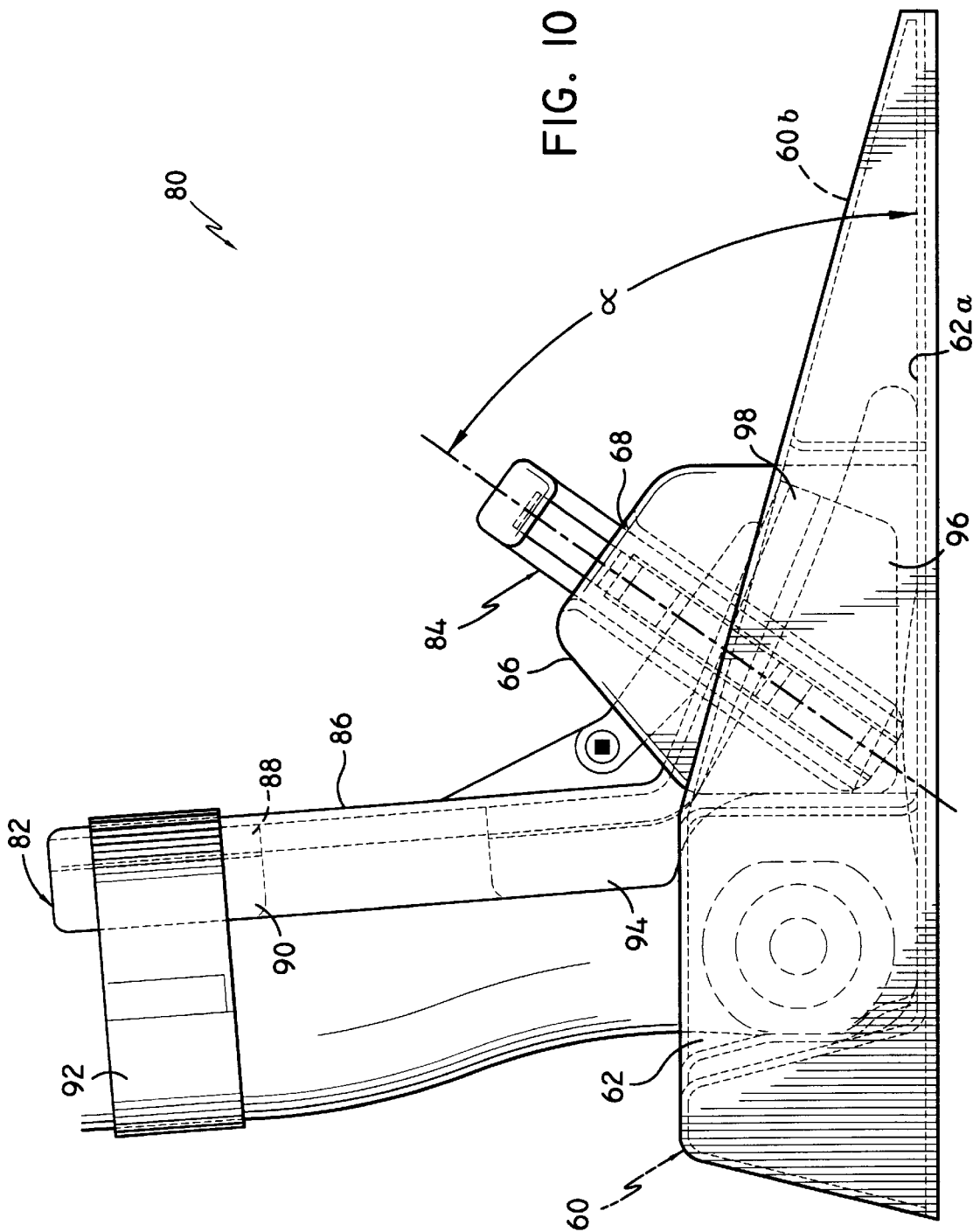
FIG. 10 is a schematic view of a patient's foot positioned in the bone measuring system of FIG. 9, and illustrating a foot bridge for maintaining the position of the foot.
Figure 11:
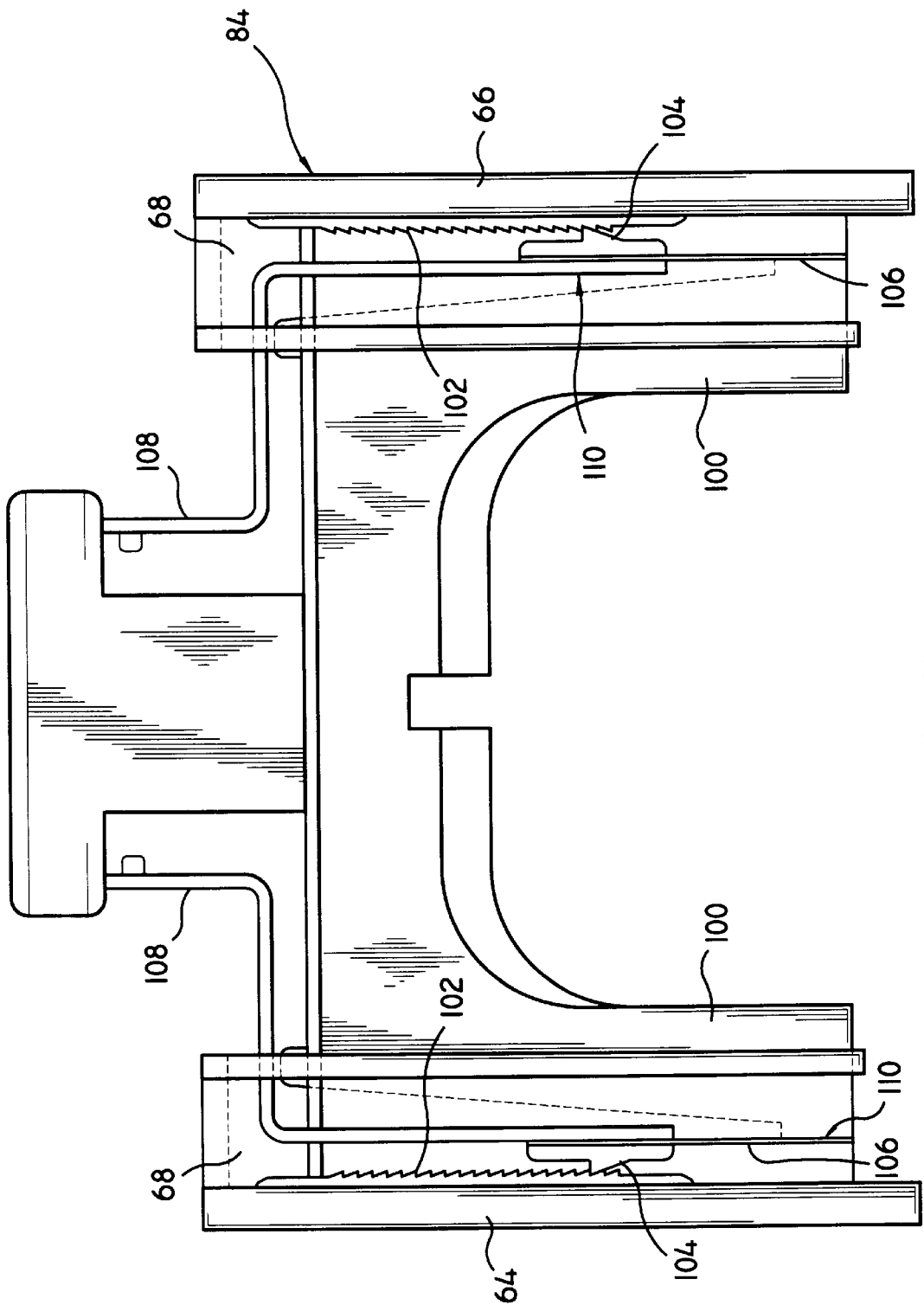
FIG. 11 is a front elevational view of the foot bridge of FIG. 10.

Referring to FIG. 9, a perspective view of an integral bone measuring system 10 is shown. In this embodiment, the system 10 has a housing 60 that is configured to firmly support, for example, a patient's foot for the ultrasound bone measurement. FIGS. 9–11 illustrate the foot support for the system 10. However, ultrasound bone measurements of other body portions of a patient such as the forearm, wrist or phalanges, may be made as well.

In the embodiment of FIGS. 8–11, the housing 60 has a base portion 60a and a support portion 60b. The support portion is configured to receive a patient's and includes support structures used to position and restrain the and lower leg in a predefined position which provides optimum coupling of ultrasonic transducer energy with the patient's ankle. The support portion 60b of housing 60 includes a well 62 configured as a universal support which receives large adult size feet as well as small children's feet, and bridge brackets 64 and 66 which include channels 68. The channels 68 are angled at a predefined angle ($\alpha$) with respect to the base 62a of the well so as to ensure stable restraint of the and leg of the patient. Preferably, the predefined angle is 55 degrees. Transducer ports 70 are located on the sides walls of the well 62, as seen in FIG. 9.

Referring to FIG. 10, a restraint member 80 has two independent sub-assemblies, namely a shin guide assembly 82 and a bridge assembly 84. The shin guide assembly 82 includes a plastic molded form 86 lined with contoured foam lining 88. The molded form 86 preferably utilizes a combination of restraints for the shin, instep, and front of the which are integrally formed into a single structure.

The molded form 86 includes shin restraint section 90 which restrains, supports, and centers the tibia against the contoured foam lining 88 using a flexible strap 92 placed around the calf muscle. The flexible strap 92 can be adjusted to secure the molded form 86 comfortably around the shin region. The shin restraint section 90 of the shin guide assembly 82 extends upward from an instep support section 94 at a predefined angle with respect to the well bottom 62a. Preferably, the predefined angle is about 95 degrees.

Referring again to FIG. 10, the front of the is restrained from lateral rotation by a restraint section 96 extending from the lower part of the instep support section 94 towards the toes. As seen in FIG. 10, the restraint section 96 has a contoured foam lining 98 which is provided to properly center the front of the as the molded form 86 is lowered to align with the correct width of the patient's. Because the thickness of the also varies laterally, the height of the restraint section 96 is typically greater near the instep than near the front of the.

Referring to FIGS. 10 and 11, the bridge assembly 84 is configured for mounting on opposing sides of the molded form 86 and for using slide blocks 100. The bridge assembly 84 is provided to attach the shin guide assembly 82 to the housing 60 and to properly align and maintain the position of the patient's. To achieve this, the slide blocks 100 are inserted into corresponding channels 68 in brackets 64 and 66 extending from the support portion 60b of housing 60. The preferred 55 degree angle of the channels 68 facilitates proper contact between the bridge assembly 84 and the instep area of different size feet, as well as, sufficient differential vertical displacement to allow the restraint section 96 to match and center varying widths of the lower.

Referring to FIG. 11, the channels 68 are lined with strips of repeating triangular ratchet teeth 102 secured to each bracket 64 and 66. The slide blocks 100 have matching ratchet teeth 104 in opposition with the teeth 102 secured to the brackets. This configuration is similar to a pawl and rachet mechanism. When the slide blocks 100 are inserted into the channels 68, the ratcheting action between teeth 102 and 104 allows the slide blocks 100 to latch at one of multiple levels to the bridge brackets 64 and 66 so as to permit selective adjustment of the shin guide assembly 82. As a result, the shin guide assembly can be adjusted to provide a comfortably fit for any size, while maintaining the proper restraint of the patient's and leg.

To facilitate release of the mating ratchet teeth 102 and 104, the ratchet teeth 104 are preferably attached to spring assembly 110 which includes leaf spring 106 mounted to the base of the slide blocks 100. To release the rachet teeth, an operator squeezes together two rigid brackets 108 of spring assembly 110 which are attached to the free ends of the springs 106. When an operator squeezes the brackets together, ratchet teeth 104 retract from teeth 102. When the teeth 104 are clear of the teeth 102 inside the channels 68, the operator can pull the slide blocks 100 out of the channels 68 to allow the patient to remove their from the well 62.

Shin guide assembly 82 may be conveniently stored for transport of the restraint member 80 by sliding the slide blocks 100 into a lowest position in the channels 68.

Figure 12:
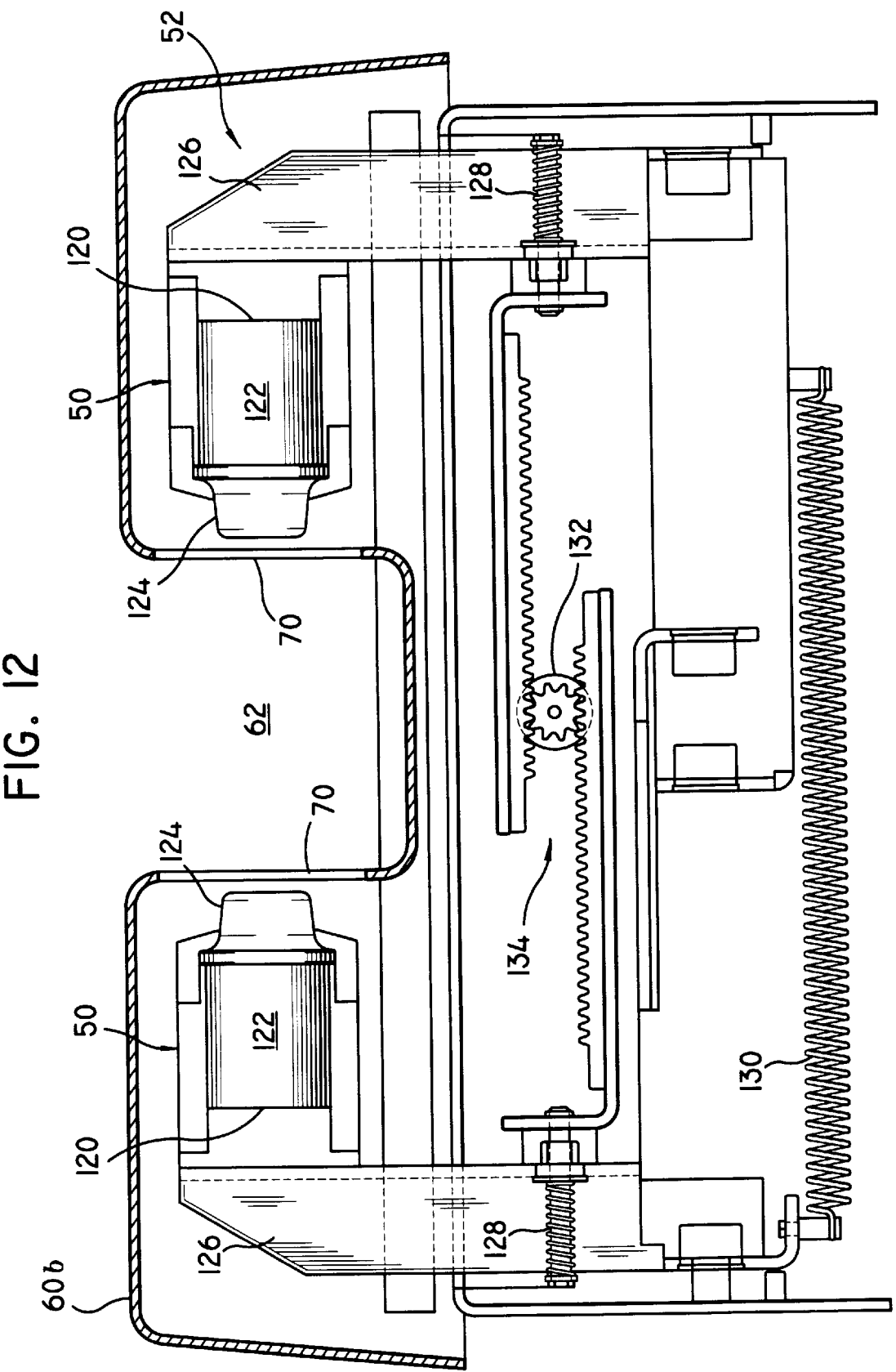
FIG. 12 is a front elevational view of a portion of the internal components of the bone measuring system of FIG. 9, and illustrating a pair of transducer assemblies movable relative to each other, and associated drive mechanisms for moving the transducers.

Referring now to FIG. 12, transducer drive mechanism 52 automatically positions transducer assemblies 50 against the patient's heel with sufficient pressure to insure ultrasonic coupling. Preferably, each transducer assembly 50 includes a transducer 120, an acoustical delay line 122 and a coupling pad 124.

Based on the quality of the signals received from the transducer assemblies 50, the coupling pressure is modified under control of controller 16, seen in FIG. 8, to insure proper operation. The quality of the signals received is determined at least in part according to the strength of the signals (i.e., the signal amplitude) and the positional data of the transducers with respect to the patient. As noted above, the position encoder 54 is utilized to determine the position of the transducers.

The transducers 120 are mounted to respective carriages 126 and are configured to slide independently along a lateral-medial axis. Respective compression springs 128 attached to the carriages 126 apply opposing lateral forces towards the center of the. In this configuration, the carriage/spring assembly is free floating and will center itself on the with equal pressure on both sides.

An extension spring 130 applies the initial pressure when the coupling pads 124 reach the patient's. To adjust the pressure in small increments, a stepper motor 132 with, for example, a rack and pinion mechanism 134 will move a finite number of steps and compress the compression springs 128 attached to the respective carriages 126. The compression springs 128 will pull the respective transducer assemblies 50 and pads 124 inward at a force proportional to the spring rate and distance translated.

As noted, the distance between the transducer assemblies 50 is continuously measured by the position encoder 54 which is mechanically linked to the motion of the transducer assemblies 50. Typically, the encoder uses a code strip mounted onto one of the carriages and an optical encoder reader mounted on the other carriage. As the distance between the transducers changes, the code strip moves between the slots of the optical encoder and the optical reader reads the lines of the code strip as the lines are traversed.

The operation of the stepper motor 132 is controlled by controller 16 according to the quality of the signals received from the transducer assemblies 50 and positional data supplied by the position encoder.

Accordingly, the transducer drive mechanism 52 under the control of controller 16 provides automatic positioning and other selectable functions. For example, the transducer drive mechanism separates the transducers 120 to allow the patient's to be moved to and from a position between the transducers 120 without interference from the transducers, positions the position encoder to a known transducer separation zero, extends the transducers 120 to a cleaning or standby position, and secures the transducers 120 in an off or shipping position.

The controller 16 determines other parameters of interest, including broadband ultrasound attenuation (BUA) and bone velocity. Also, the controller 16 calculates the speed of the ultrasonic signals (SOS) through, for example, the using the distance between the transducers determined by the position encoder 54. The controller combines the results of the BUA and SOS measurements to obtain a bone mass measurement. Apparatus for measuring bone mass using ultrasound are known in the art. Such an apparatus is disclosed in, for example, U.S. Pat. No. 4,774,959 to Palmer et al., which is incorporated herein in its entirety by reference.

The controller 16 uses temperature readings from temperature sensor 56 to improve the accuracy of the position encoder measurements and correct for temperature dependent inaccuracy in the ultrasound measurement. For example, the controller 16 accounts for liner expansion of the encoder strip by applying a temperature dependent term to the data supplied by the position encoder 54. Additionally, the controller 16 applies a temperature dependent term to correct an estimation of the time delay through the delay line 122 and the coupling pad 124. Furthermore, the controller 16 uses the temperature reading to determine if the apparatus is operating within the specified environmental range allowed, and if not, the operator is informed that the apparatus is not ready to be used.

Several features of the elastomer coupling pads 124 which provide efficient coupling of ultrasonic energy will now be described. The acoustic impedance of the material of the pads 124 is matched to the acoustic impedance of human skin to provide a minimal loss of power and reduce extraneous reflections.

The coupling pads 124 also provide a waveguide function to collimate the acoustic beam a sufficient distance along the propagation axis to allow the wavefronts to evolve onto a more uniform intensity pattern. To this end, the acoustical delay lines 122 are provided to allow the wavefronts to evolve from the granular near field pattern to a smoother far field pattern before entering the body.

The pads 124 are chosen to have a durometer corresponding to a sufficiently flexible waveguide that can partially conform to the shape of and provide some comfort to the patient. The shape of the pads 124 preferably conform to the heel so as to eliminate any air gaps between the heel and pad. The surfaces of the pads 124 which contact the transducers 120, the delay line, or the patent's skin may be shaped to expel air bubbles from the contact area when pressure is applied. The surface of the pad that contacts the patient's skin may be shaped at an angle other than orthogonal to the propagation axis to reduce the acoustic reflection at the pad-to-skin interface by spreading the reflected energy over time and position. Other configurations of the pad also provide effective coupling of the ultrasonic energy. For example, the pad may be conically shaped such that when the narrow portion of the conical shape engages the heel and is subsequently compressed, air is force from the contact surface of the pad.

The material of the pads 124 is required to be compatible with coupling gel and non-irritating to the skin. One material of choice at this time is CIBA polyurethane (TDT 178-34) mixed with additive to provide a cured durometer of approximately 10 to 15 Shore A.

Commercially available coupling gel may be used between the skin and coupling pads. One implementation of the invention uses petroleum jelly as a coupling gel.

The ultrasound coupling gel that is commonly used to efficiently couple ultrasonic energy between the skin and transducers also may be eliminated by using a self wetting material such as Parker Laboratory Aquaflex pads. In one implementation of the design, self wetting coupling pads would be used as a disposable, or single use device, eliminating concerns about sanitation.

An alternative embodiment for the ultrasonic densitometric bone measuring unit is described in commonly owned U.S. Pat. No. 5,134,999 to Osipov which is incorporated herein in its entirety by reference.

Referring to FIG. 13, an exemplary embodiment of an individual (or stand alone) biochemical bone measuring unit is shown. In this embodiment, the biochemical bone measuring unit 160 includes a housing 162 which is preferably constructed for hand held operation. Typically, the housing is dimensioned similar to a hand held calculator and includes a display 164, user operable switches 38 and 40, and an access port 168 for receiving a sample strip (described in more detail below). In the embodiment where the reader portion is disposable, access port 168 is provided to facilitate the transfer through, for example capillary distribution, a bodily fluid sample onto a strip test. A printer paper port 170 may optionally be provided to discharge a printout of the measured bone turnover data.

The stand alone biochemical bone measuring unit 160 is preferably a processor controlled unit powered by battery 172, seen in phantom in FIG. 3. Similar to the above described biochemical bone measuring unit, a controller 16 includes a microprocessor or microcontroller, memory (e.g., ROM and RAM), stored programs (e.g., system and application programs) for controlling the operation of the microprocessor or microcontroller, for performing a strip sample reading function, and for performing system verification procedures, such as self-test and calibration procedures. The controller 16 also includes input/output circuitry which permits the controller to interact with an alphanumeric display 22, a printer 20, control buttons 38 and 40, and strip sample reading circuit 24. The circuitry for the stand alone unit is similar to that shown in FIG. 3 and described above. A communication port 21, seen in FIG. 7, is provided to permit data communication between, for example, the biochemical bone measuring unit and an external computer.

The operation of the biochemical bone measuring unit of the stand alone embodiment is similar to the operation described above with regards to the integral unit. To activate the system verification procedures, either control button may be depressed a predefined number of times to perform the desired function. To illustrate, control button 40 may be depressed three times in rapid succession which may cause a system self-test procedure to be executed. Alternatively, a keypad may be substituted for the control buttons 38 and 40 and connected to the processor. Using the keypad an operator may type in the instruction to execute a particular function, or the keypad may have dedicated function keys which when depressed cause the execution of the desired function.

Preferably, in this embodiment the biochemical bone measuring unit 160 is configured to detect the presence of one or more analytes on a pre-formatted strip sample. As described above, the strip sample is typically the result of a quantitative in-vitro diagnostic strip test performed in blood or urine. The strip sample can be measured, for example, as discussed in the embodiments above.

Figure 14:
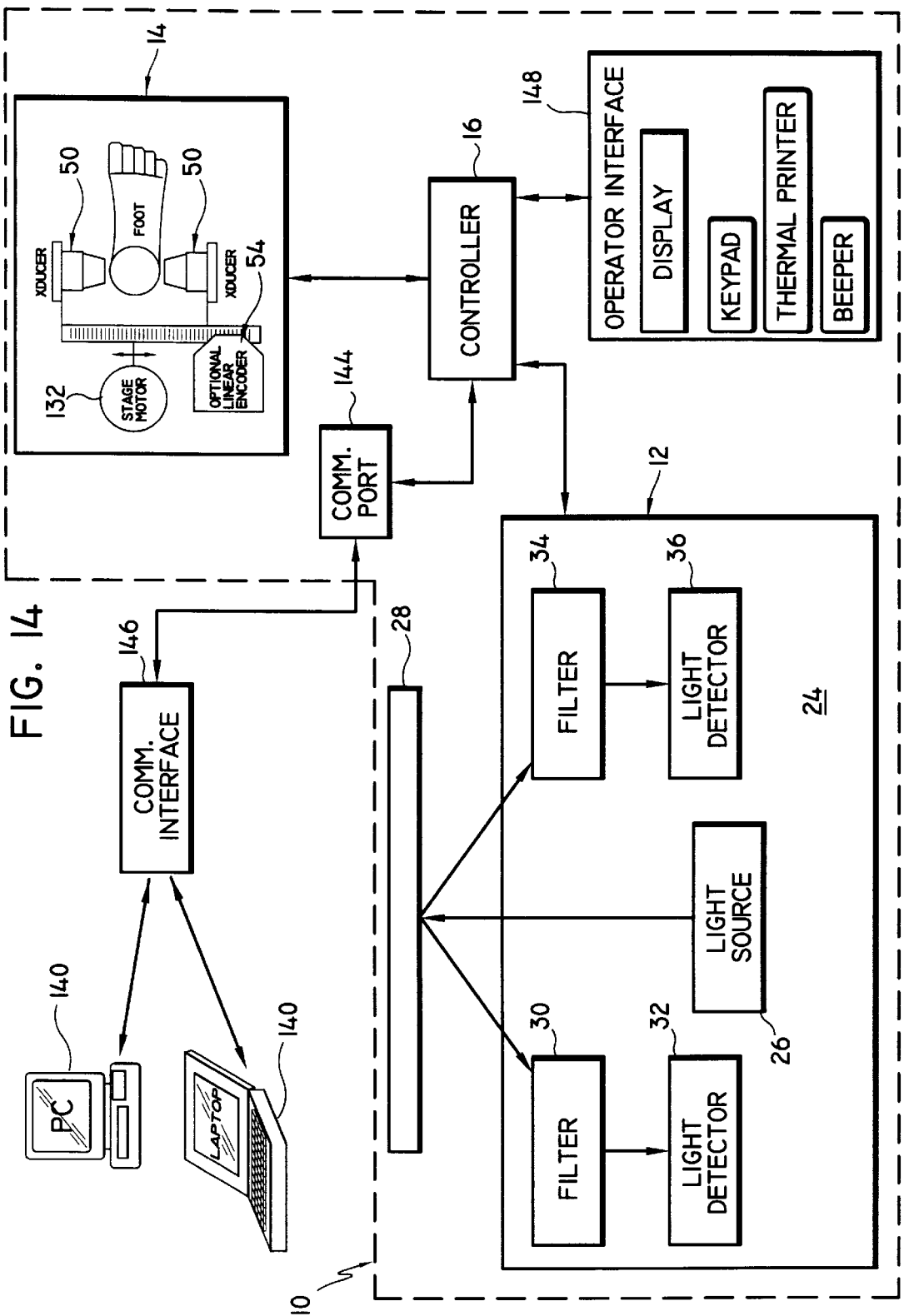
FIG. 14 is a block diagram of an alternative embodiment of the bone measuring system according to the present invention.
Figure 15:
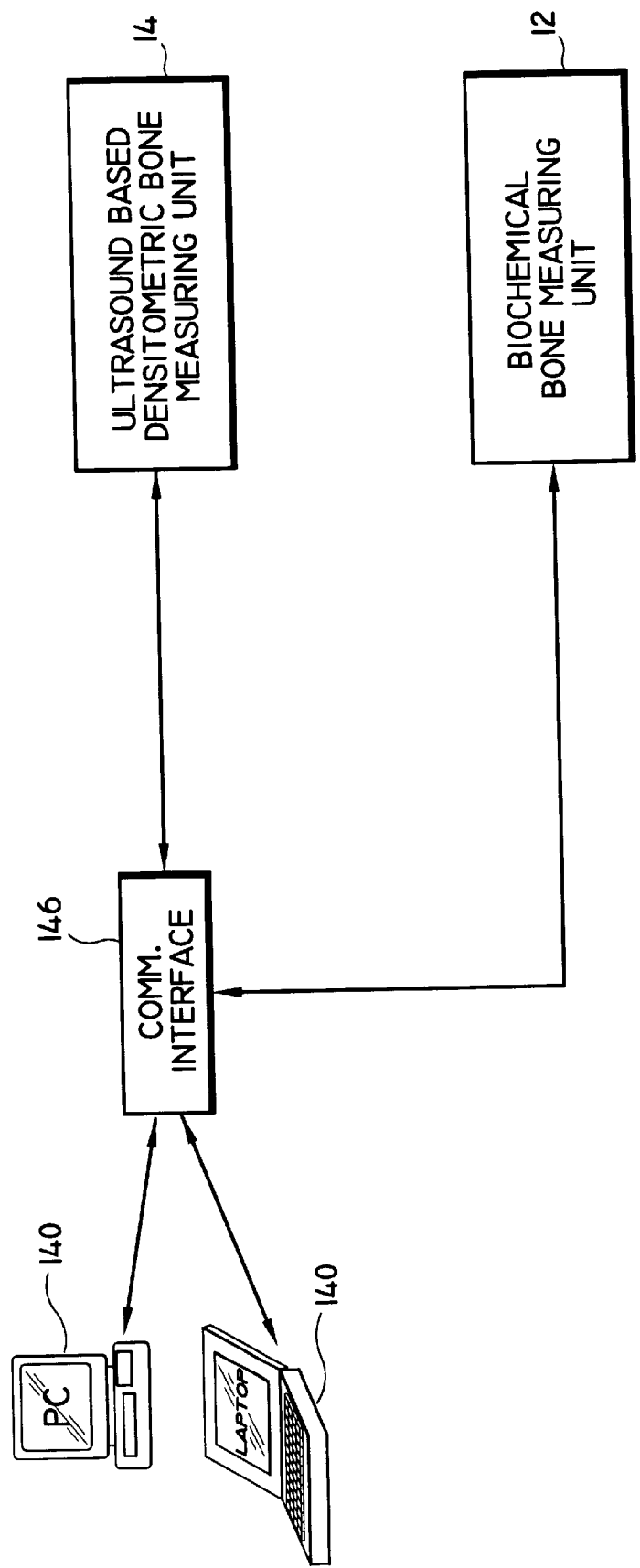
FIG. 15 is a block diagram of an alternative embodiment of the bone measuring system according to the present invention, and illustrating an ultrasonic densitometric bone measuring unit and a biochemical bone measuring unit coupled to a computer by a communication interface.
Figure 16:
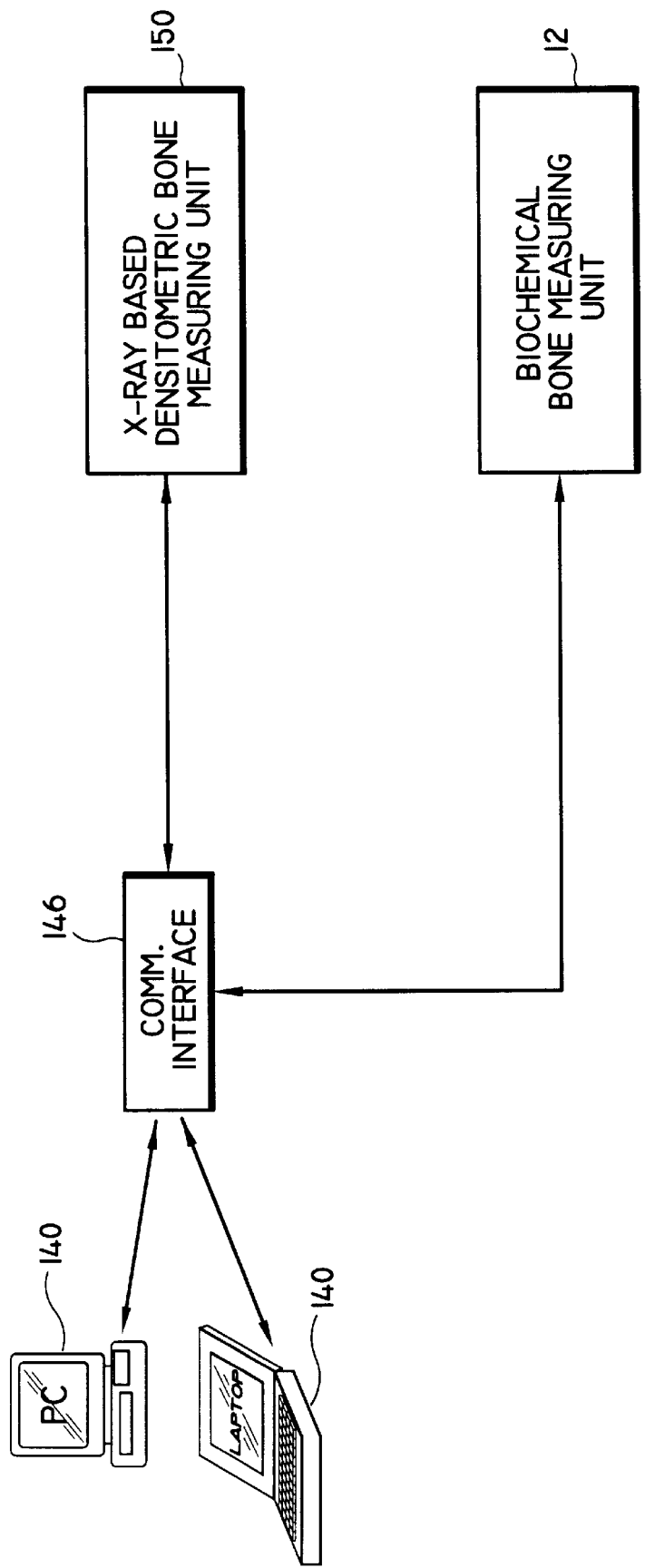
FIG. 16 is a block diagram of another alternative embodiment of the bone measuring system of the present invention, and illustrating an x-ray based densitometric bone measuring unit and a biochemical bone measuring unit coupled to a computer by the serial communication interface.

Referring now to FIGS. 14–16, alternative embodiments of the bone measuring system are shown. In FIG. 14, the bone measuring system 10, described above, and one or more external computers 140 (e.g., a personal or laptop computer). As seen in FIG. 14, bone measuring system 10 is coupled to the computer 140 via communication port 144 and serial port 146. The communication port 144 is connected to controller 16 and is preferably configured for serial and/or parallel communications, e.g., RS-232 standard communications. In this configuration, the bone characteristic data determined by controller 16 can be downloaded to computer 140 for subsequent processing. Further, an operator can send instruction data to system 10 from computer 140. For example, computer 140 could be used to send instructions to controller 16 to perform the biochemical assessment of bone characteristics (e.g., the strip sample measurement procedure), to perform the densitometric assessment of bone characteristics (e.g., the bone mass measuring procedure), and to instruct the controller 16 to transfer the measured data to the computer for subsequent processing. In this embodiment, the bone measuring system 10 includes the biochemical bone measuring unit 12 with the strip sample reading circuit 24 and the ultrasound bone measuring unit 14 in a single housing for use in, for example, a practitioner's office. The strip sample reading circuit 24 is similar to that described hereinabove and for clarity will not be repeated. The ultrasound bone measuring unit 14 includes the transducer assemblies 50, the position encoder 54 and the stepper motor 132 which operate in a similar manner as described above. An operator interface 148 is located on the housing of the system 10 and may include a display, keyboard, printer access port and a beeper.

In FIG. 15, the bone measuring system illustrated includes a biochemical bone measuring unit 12 and an ultrasound bone measuring unit 14, each coupled to computers 140 through for example a serial communication interface 146. Alternatively, data communications between the biochemical bone measuring unit, ultrasound bone measuring unit and the computers may be across a local area network (e.g., ETHERNET or token ring), a wide area network (WAN) or using wireless data transmission techniques such as RF or infra red. In this embodiment, each module is a separate unit having an independent controller 16 connected to the internal components described above. Each controller 16 can control the operation of each unit 12 or 14, or the controllers 16 in this embodiment can be communication processors which are used to transmit, receive and/or format bone characteristic data and instruction between the computers and/or the main controller and each unit.

The embodiment of FIG. 16 is similar to the embodiment of FIG. 15 except that an x-ray based densitometric bone measuring unit 150 is used to measure bone density. The x-ray unit 150 may include a controller connected to an x-ray source and an x-ray detector and to communication circuitry which receives data from the main controller, receives data from the x-ray detector and transmits the x-ray data to the main controller for processing. A suitable x-ray unit is the model QDR 4500 manufactured by Hologic Inc.

Figure 17A:
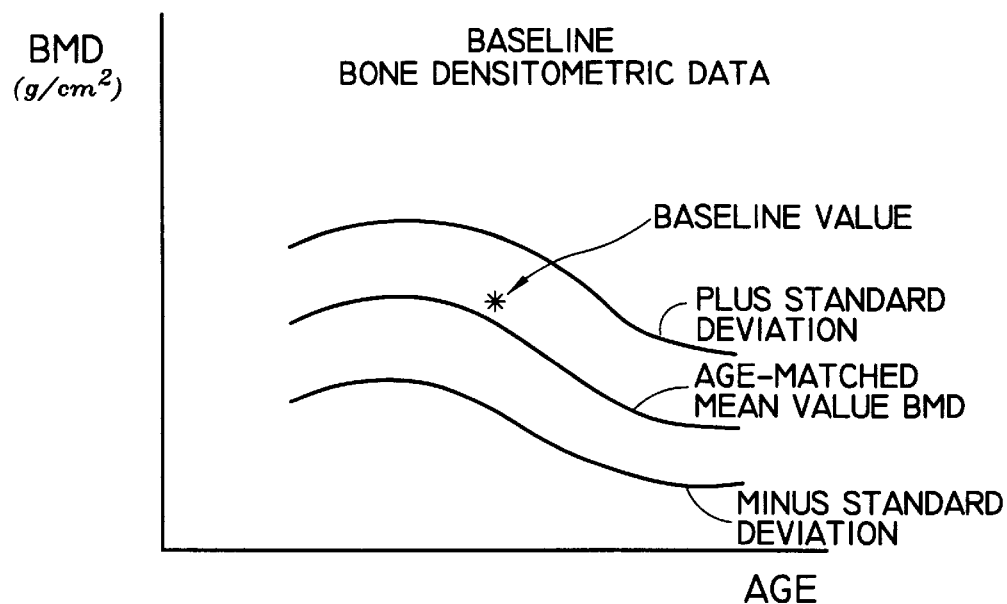
FIGS. 17a, 17b, 18a, 18b and 19 are exemplary computer generated graphical displays, illustrating baseline, monitoring/follow-up and dynamic displays for providing a practitioner with graphical results of the bone assessments.
Figure 17B:
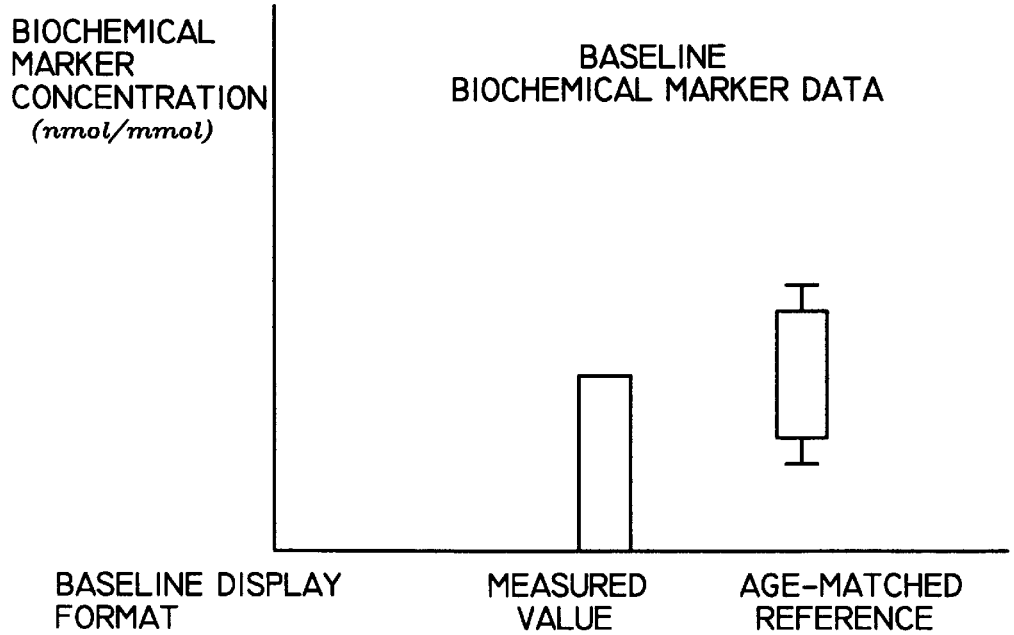
Figure 18A:
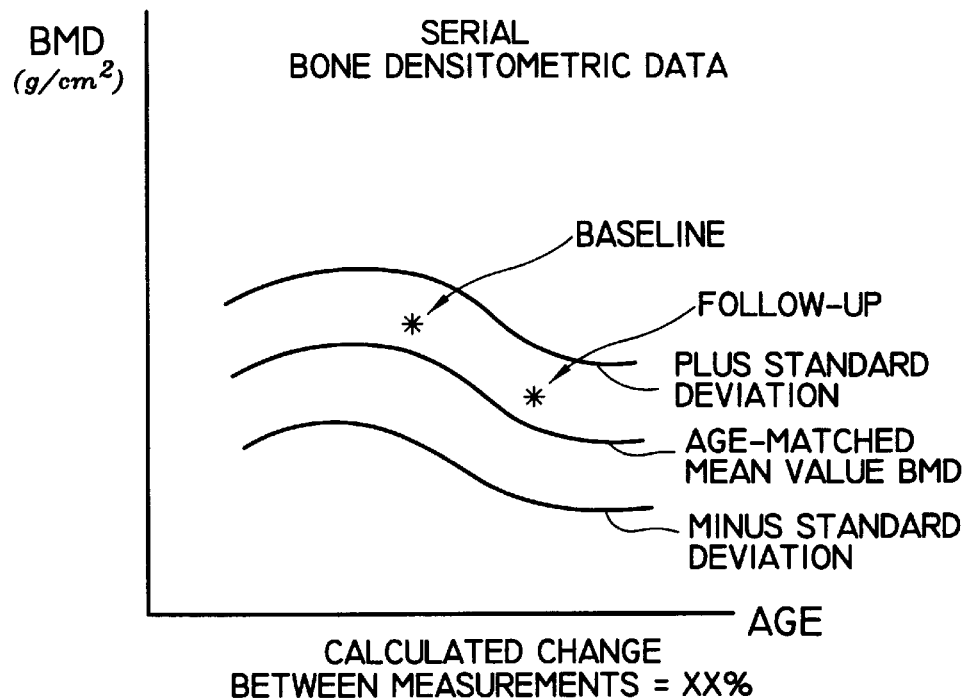
Figure 18B:
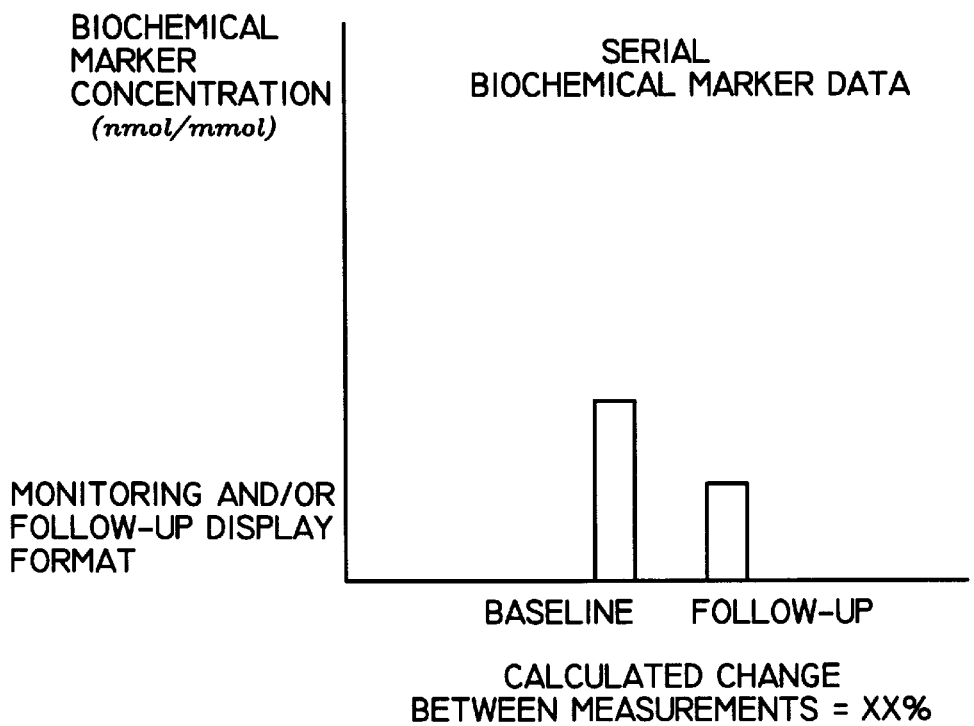
Figure 19:
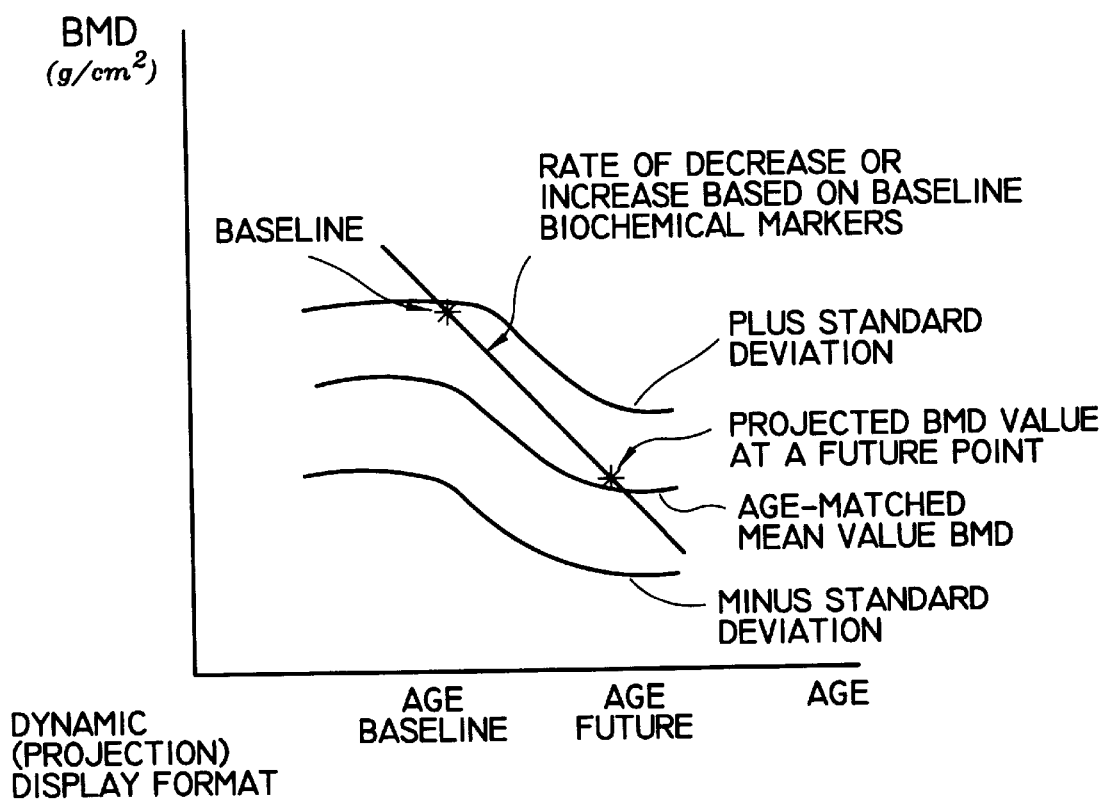

FIGS. 17–19 provide various baseline, monitoring and projection format displays which may be displayed by computer 140. FIG. 17a provides an exemplary graph of baseline bone densitometric data defined by bone mineral density versus the age of a patient. FIG. 17b provides an exemplary graph of baseline biochemical marker data defined by biochemical marker concentration (representing bone resorption, formation or net bone turnover) compared to typical age matched reference levels. FIG. 18a provides an exemplary graph of serial bone densitometric data defined by bone mineral density versus the age of the patient which illustrates a rate of change between measurements. FIG. 18b provides an exemplary graph of serial baseline biochemical marker data defined by biochemical marker concentration (representing bone resorption, formation or net turnover) compared to the concentration at a follow-up visit, which illustrates a rate of change between measurements. FIG. 19 provides an exemplary dynamic graph of bone densitometric data and biochemical marker data which illustrates a baseline BMD value based on densitometric data and a slope representing a rate of increase or decrease in bone density which is based on baseline biochemical markers to provide a projected BMD value of the patient at a future age.

It will be understood that various modifications can be made to the embodiments of the present invention herein disclosed without departing from the spirit and scope thereof. For example, various size housings are contemplated, as well as various type of transducers and various types of mechanisms to move the transducers. Various systems for detecting the concentration of analytes are also contemplated. For example, various light sources are contemplated such as LED, laser, incandescent and fluorescent light sources, as well as various detection techniques used to detect the light reflected by or emitted from the strip sample such as reflectance, sample fluorescence and absorption. Therefore, the above description should not be construed as limiting the inventions but merely as exemplifications of preferred embodiments thereof. Those skilled in the art will envision other modifications within the scope and spirit of the present invention as defined by the claims appended hereto.

What is claimed is:

1. A method of projecting bone characteristics of a patient, comprising:

reading a strip sample to derive therefrom current bone turnover data by directing light toward the strip sample and detecting light from the strip sample and generating therefrom signal data indicative of a predefined color wavelength and defining said current bone turnover data associated with the patient;

obtaining current bone density data from the patient; and processing said current bone density data and said current turnover data to derive a projection of future bone characteristics based on directly combining said current bone density data and said current bone turnover data.

2. A bone measuring system, which comprises:

means for processing data;

a first bone measuring unit coupled to said processing means and configured to obtain dynamic bone characteristic data and to transfer said dynamic bone characteristic data to said processing means; and a second bone measuring unit coupled to said processing means and configured to obtain static bone characteristic data, and to transfer said static bone characteristic data to said processing means;

said processing means directly combining said dynamic bone characteristic data and said static bone characteristic data to derive bone parameter data.

3. The system according to claim 2, wherein said dynamic bone characteristic data is obtained from a strip sample.

4. The system according to claim 2, wherein said dynamic bone characteristic data comprises bone resorption data.

5. The system according to claim 2, wherein said dynamic bone characteristic data comprises bone formation data.

6. The system according to claim 2, wherein said static bone characteristic data comprises bone density data.

7. The system according to claim 2, wherein said processing means processes said dynamic and static bone characteristic data from said first and second bone measuring units for subsequent numerical or graphical display.

8. The system according to claim 2, wherein said processing means processes said dynamic and static bone characteristic data from said first and second bone measuring units and provides said bone parameter data in the form of projections of bone characteristics.

9. The system according to claim 2, wherein said processing means processes said dynamic and static bone characteristic data from said first and second bone measuring units and provides said bone parameter data in the form of risk determinations of bone related injuries.

10. The system according to claim 9, wherein said risk determination includes fracture risk.

11. The system according to claims 2, wherein said dynamic bone characteristic data comprises bone resorption and bone formation data and said processing means processes said bone characteristic data to determine bone turnover.

12. The system according to claim 2, wherein said first bone measuring unit is a unit measuring biochemical markers of bone.

13. The system according to claim 2, wherein said second bone measuring unit is a densitometric bone measuring unit.

14. The system according to claim 13, wherein said densitometric bone measuring unit is an ultrasound bone measuring unit.

15. The system according to claim 13, wherein said densitometric bone measuring unit is an x-ray based unit having an x-ray source, an x-ray detector and a controller.

16. The system according to claim 2, wherein said first bone measuring unit is coupled to said processing means so that data is transferred between said processing means and said first bone measuring unit serially.

17. The system according to claim 2, wherein said second bone measuring unit is coupled to said processing means so that data is transferred between said processing means and said second bone measuring unit serially.

18. The system according to claim 2, wherein said processing means comprises a computer.

19. A bone measuring system, which comprises:

means for processing data;

dynamic bone measuring means coupled to said processing means, for obtaining dynamic bone characteristic data and transferring said dynamic bone characteristic data to said processing means; and static bone measuring means coupled to said processing means, for obtaining static bone characteristic data and for transferring said static bone characteristic data to said processing means;

said processing means selectively directly combining said dynamic and static bone characteristics.

20. The system according to claim 19, wherein said dynamic bone characteristic data is obtained from strip sample means.

21. The system according to claim 19, wherein said dynamic bone characteristic data comprises bone resorption data.

22. The system according to claim 19, wherein said dynamic bone characteristic data comprises bone formation data.

23. The system according to claim 19, wherein said static bone characteristic data comprises bone density data.

24. The system according to claim 19, wherein said processing means processes said dynamic and static bone characteristic data from said dynamic and static bone measuring means, for subsequent numerical or graphical display.

25. The system according to claim 19, wherein said processing means processes said dynamic and static bone characteristic data from said dynamic and static bone measuring means and provides as an output projections of bone characteristics.

26. The system according to claim 19, wherein said processing means processes said dynamic and static bone characteristic data from said dynamic and static bone measuring means and provides as an output risk determinations of bone related injuries.

27. The system according to claim 26, wherein said risk determination includes fracture risk.

28. The system according to claims 19, wherein said dynamic bone characteristic data comprises bone resorption and bone formation data and said processing means processes said bone characteristic data to determine bone turnover.

29. The system according to claim 19, wherein said dynamic bone measuring means comprises a unit measuring biochemical markers of bone.

30. The system according to claim 19, wherein said static bone measuring means comprises densitometric bone measuring means.

31. The system according to claim 30, wherein said densitometric bone measuring means comprises an ultrasound bone measuring unit.

32. The system according to claim 30, wherein said densitometric bone measuring means comprises an x-ray based unit having an x-ray source, an x-ray detector and a controller.

33. The system according to claim 19, wherein said dynamic bone measuring means is coupled to said processing means so that data is transferred between said processing means and said dynamic bone measuring means serially.

34. The system according to claim 19, wherein said static bone measuring means is coupled to said processing means so that data is transferred between said processing means and said static bone measuring means serially.

35. The system according to claim 19, wherein said processing means comprises a computer.

36. A method for projecting bone characteristics of a patient, comprising:
reading a strip sample by directing energy toward the strip sample and detecting energy resulting from impingement of said directed energy with the strip sample and generating therefrom dynamic bone characteristic data associated with the patient;
obtaining static bone characteristic data for the patient; and
projecting future bone characteristics based on directly combining said static bone characteristic data and said dynamic bone characteristic data.

37. The method according to claim 36, wherein said dynamic bone characteristic data comprises bone resorption data.

38. The method according to claim 36, wherein said dynamic bone characteristic data comprises bone formation data.

39. The method according to claim 36, wherein said static bone characteristic data comprises bone density data.

40. The method according to claim 36, wherein said dynamic bone characteristic data comprises bone formation and bone resorption data.

41. The method according to claim 40 further comprising determining bone turnover based on a relationship between said bone formation and bone resorption dynamic bone characteristic data.

42. The method according to claim 41, wherein the step of projecting future bone characteristics is based on said static bone characteristic data and said bone turnover data.

43. A method of obtaining bone characteristic estimates comprising:
obtaining first bone data from a patient through a measurement free of the use of ionizing radiation or ultrasound energy;
obtaining second bone data from the patient through a measurement that includes the use of at least one of ionizing radiation and ultrasound energy;
computer-processing said data in a process free of the use of neural networks to provide bone characteristic estimates based on both the first and the second bone data.

44. A method as in claim 42 in which said obtaining of first bone data comprises obtaining bone data from biochemical marker testing.

45. A method as in claim 44 in which said computer-processing of said data comprises directly combining said first and second bone data to provide said bone characteristics estimates, and wherein said estimates comprise predictions of future bone characteristics of the patient.

46. A system for obtaining bone characteristic estimates comprising
a first measuring device producing first bone data from a patient through a measurement free of the use of ionizing radiation or ultrasound energy;
a second measuring device producing second bone data from the patient through a measurement that includes the use of at least one of ionizing radiation and ultrasound energy;
a computerized processing unit coupled to said first and second measuring devices to receive said data therefrom and to process the received data in a process free of the use of neural networks to provide bone characteristic estimates based on both the first and the second bone data.

* * * * *